United States Patent [19]

Sakai et al.

[11] Patent Number: 4,555,479
[45] Date of Patent: Nov. 26, 1985

[54] COLOR PHOTOGRAPHIC LIGHT-SENSITIVE MATERIAL

[75] Inventors: Nobuo Sakai; Masaki Okazaki; Yoshio Inagaki, all of Kanagawa, Japan

[73] Assignee: Fuji Photo Film Co., Ltd., Kanagawa, Japan

[21] Appl. No.: 614,091

[22] Filed: May 25, 1984

[30] Foreign Application Priority Data

May 25, 1983 [JP] Japan .................................. 58-92082

[51] Int. Cl.⁴ .......................... G03C 7/40; G03C 7/26
[52] U.S. Cl. ..................................... 430/372; 430/387; 430/393; 430/505; 430/551; 430/555; 430/558
[58] Field of Search ............... 430/551, 372, 555, 387, 430/505, 393, 558

[56] References Cited

U.S. PATENT DOCUMENTS

| | | | |
|---|---|---|---|
| 2,324,123 | 7/1943 | Weissberger | 430/372 |
| 2,487,569 | 11/1949 | Mackey | 430/372 |
| 4,268,592 | 5/1981 | Tschopp | 430/555 |
| 4,310,623 | 1/1982 | Watanabe et al. | 430/551 |
| 4,378,426 | 3/1983 | Lok et al. | 430/551 |
| 4,463,085 | 7/1984 | Mitsui et al. | 430/555 |

*Primary Examiner*—J. Travis Brown
*Attorney, Agent, or Firm*—Sughrue, Mion, Zinn, Macpeak & Seas

[57] ABSTRACT

A silver halide color photographic light-sensitive material comprising a support having coated thereon at least one silver halide emulsion layer, the color photographic light-sensitive material having at least one layer containing at least one 2-equivalent magenta coupler of the 5-pyrazolone type represented by the following general formula (I):

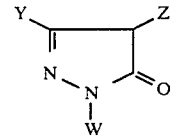

wherein W represents a phenyl group substituted with at least one substituent selected from the group consisting of a halogen atom, an alkyl group, an alkoxy group, an alkoxycarbonyl group and a cyano group; Y represents an acylamino group or an anilino group; and Z represents a group capable of being released upon coupling, and at least one compound represented by the following general formula (II):

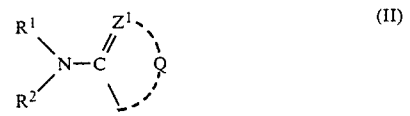

wherein $R^1$ and $R^2$, which may be the same or different, each represents a hydrogen atom, an alkyl group or an aryl group, provided that both $R^1$ and $R^2$ do not represent hydrogen atoms at the same time; $Z^1$ represents a methine group, a substituted machine group or the group —N=; and Q represents an atomic group which contains a nitrogen atom, a sulfur atom or an oxygen atom and is necessary to form a 5-membered or a 6-membered heterocyclic ring together with the group

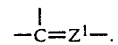

The silver halide color photographic light-sensitive material can provide an excellent magenta color image without the occurrence of stain, even when the color photographic material is processed in a processing solution under the running condition.

21 Claims, No Drawings

COLOR PHOTOGRAPHIC LIGHT-SENSITIVE MATERIAL

FIELD OF THE INVENTION

The present invention relates to a color photographic light-sensitive material containing a 2-equivalent magenta coupler and, particularly, to a method for prevention of stain which occurs during development processing of a color photographic light-sensitive material containing a 2-equivalent magenta coupler.

BACKGROUND OF THE INVENTION

Various pyrazolone derivatives are known as magenta dye forming couplers (hereinafter referred to as a magenta coupler). However, pyrazolone derivatives generally used for photographic light-sensitive materials are 4-equivalent couplers. Such compounds theoretically require the development of four mols of silver halide for forming one mol of a dye by reacting with an aromatic primary amine developing agent. However, pyrazolones having an active methylene group substituted with a group which can be released by oxidative coupling with an oxidation product of a primary amine developing agent require development of only two mols of silver halide. In addition, the 4-equivalent pyrazolone derivatives have a low color forming efficiency (conversion rate of the coupler into the dye) and generally form only a ½ mol or so of the dye per mol of the coupler.

As a means for improving the color forming efficiency by decreasing the amount of silver halide required for development, utilization of 2-equivalent pyrazolone magenta couplers has been proposed. Examples of pyrazolone derivatives which release an oxygen atom include compounds having an aryloxy group in the 4-position of a 5-pyrazolone as described in U.S. Pat. No. 3,419,391 and compounds having an alkyloxy group as described in Japanese Patent Publication No. 46453/78.

Examples of pyrazolone derivatives which release a nitrogen atom include compounds having an imidazolyl group, a pyrazolyl group or a triazlyl group in the 4-position of a 5-pyrazolone as described in U.S. Pat. Nos. 4,076,533 and 4,241,168, compounds having a pyridonyl group or a 2-oxopiperidinyl group as described in U.S. Pat. No. 4,220,470 and compounds having a sulfonamido group as described in U.S. Pat. No. 4,237,217.

Further, examples of pyrazolone derivatives which release a sulfur atom include compounds having a heterocyclic thio group or an arylthio group in the 4-position of a 5-pyrazolone as described in U.S. Pat. Nos. 3,227,554 and 4,263,723, Japanese Patent Publication No. 34044/78, compounds having a thiocyano group as described in U.S. Pat. No. 3,214,437 and compounds having a dithiocarbamate group as described in U.S. Pat. No. 4,032,346. These compounds are advantageous in that most of them can be synthesized from 4-equivalent pyrazolone couplers in one step. Also, these compounds are advantageous in view of photographic sensitivity and equivalency. It has been found that compounds having a 2-alkoxyarylthio group in the 4-position of a 5-pyrazolone have exceptionally superior properties among couplers of the type which release an arylthio group. In addition, magenta color images formed from the couplers having a 2-alkoxyarylthio group have good fastness to light, while the light fastness of magenta color images formed from conventional couplers having an arylthio group is remarkably inferior.

However, these 2-equivalent magenta couplers do not sufficiently eliminate stains (increase in color density in unexposed areas) which are formed by development processing.

The stains occurring in unexposed areas of a silver halide color photographic light-sensitive material are undesirable and are a determining factor with respect to whether whiteness of the non-image areas is good or bad. Further, the stains adversely affect the color turbidity of the images and injure the visual sharpness of the images. Particularly, in case of reflective photographic materials, for example, photographic color papers, the reflective density of the stains is theoretically emphasized several times that of the transmission density. Therefore, the stains are very important factors since a slight degree of stain still injures the image quality.

The stains in the silver halide color photographic light-sensitive materials are roughly classified into four groups, depending on the cause of the stain. First is a stain which is formed after the production of the photographic light-sensitive material and before the processing thereof due to heat or humidity. Second is a stain caused by development fog of the silver halide. Third is a stain based on color contamination due to color couplers in a development processing solution (for example, aerial fog, etc.) or a stain due to a dye formed by the reaction with a coupler of an oxidized developing agent which is formed by oxidation of a developing agent remaining in the silver halide emulsion layer by a bleach solution or oxygen in the air, etc. (for example, bleaching stain, etc.). Fourth is a stain based on changes in photographic materials after development processing with the passage of time due to light, humidity or heat. The present invention relates to stains due to the development processing of photographic materials containing 2-equivalent magenta couplers, i.e., the present invention relates to the third and fourth types of stains described above.

It is unusual to prepare a new solution for development processing after every development processing. In practice, the solution is replenished by adding a replenishing developing solution in an amount which depends on the amount of photographic materials developed. However, the composition of the solution cannot be maintained merely by adding components which are consumed by development.

In general, solutions for development processing include a color developing solution, a stopping solution, a bleaching solution, a fixing solution or a bleach-fixing (blixing) solution, etc. Since the processing temperature is maintained at a high temperature such as from 31° C. to 43° C., the compositions of the processing solutions can be changed by several factors. For example, components such as the developing agent, etc., are subjected to decomposition over a long period of time or to oxidation when brought in contact with the air. It is also possible for the components contained in the photographic light-sensitive materials to be dissolved out and accumulated in the solution during the processing of the photographic light-sensitive materials. In addition, the processing solution may be taken into the following bath by becoming attached to the photographic material. Thus, the processing solution becomes a so-called running solution. To eliminate such problems, a replenishment procedure in which lacking chemicals are supplementarily added to the solution and a regeneration procedure in which undesirable components are removed are carried out, but such procedures are still unacceptable.

Photographic light-sensitive materials containing 2-equivalent magenta couplers have a high tendency to form stains in a running solution. However, the occurrence of such stains generally cannot be prevented by techniques heretofore known. An example of one effective method for preventing such stains involves the incorporation of a reducing agent, particularly, an alkylhydroquinone (for example, those as described in U.S. Pat. Nos. 3,935,016 and 3,960,570) into a photographic light-sensitive material, particularly, an emulsion layer wherein the stains are formed. It is also known that a chroman, a coumaran (for example, those as described in U.S. Pat. No. 2,360,290), a phenol type compound (for example, those as described in Japanese Patent Application (OPI) No. 9449/76 (the term "OPI" as used herein refers to a "published unexamined Japanese patent application")), etc., are effective. Furthermore, a sulfinic acid type polymer is known as being effective as described in Japanese Patent Application (OPI) No. 151937/81. However, these known techniques cannot provide a sufficiently good effect against processing stain due to 2-equivalent magenta couplers, in particular, processing stain due to an exhausted solution, even though some effect is obtained.

SUMMARY OF THE INVENTION

An object of the present invention is, therefore, to provide a method for preventing the occurrence of stain when a photographic light-sensitive material containing a 2-equivalent magenta coupler is subjected to development processing, particularly, a method for completely preventing the occurrence of stain in a solution for development processing under running conditions.

Another object of the present invention is to provide a photographic light-sensitive material in which a 2-equivalent magenta coupler is used and the amount of silver contained is reduced and good sharpness is obtained as a result of development processing.

Other objects of the present invention will become apparent from the following detailed description and examples.

The above-described objects of the present invention can be attained by use of a silver halide color photographic light-sensitive material comprising a support having coated thereon at least one silver halide emulsion layer, the color photographic light-sensitive material having at least one layer (preferably the silver halide emulsion layer) containing at least one 2-equivalent magenta coupler of the 5-pyrazolone type represented by the following general formula (I):

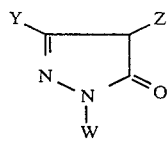

wherein W represents a phenyl group substituted with at least one halogen atom, an alkyl group, an alkoxy group, an alkoxycarbonyl group or a cyano group; Y represents an acylamino group or an anilino group; and Z represents a group capable of being released upon coupling, and at least one compound represented by the following general formula (II):

wherein $R^1$ and $R^2$, which may be the same or different, each represents a hydrogen atom, an alkyl group or an aryl group, provided that both $R^1$ and $R^2$ do not represent hydrogen atoms at the same time; $Z^1$ represents a methine group (including a substituted methine group) or the group —N=; and Q represents an atomic group which contains a nitrogen atom, a sulfur atom or an oxygen atom and is necessary to form a 5-membered or a 6-membered heterocyclic ring together with the group

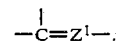

DETAILED DESCRIPTION OF THE INVENTION

In the general formula (I), preferred examples of the group capable of being released upon coupling represented by Z include an aryloxy group, an alkoxy group, a heterocyclic oxy group, a silyloxy group, a phosphonoxy group, an alkylthio group, an arylthio group, a heterocyclic thio group, an acylthio group, a thiocyano group, an aminothiocarbonylthio group, an acylamino group, a sulfonamido group, an alkoxycarbonylamino group, an aryloxycarbonylamino group or a nitrogen-containing heterocyclic group which is connected to the active position of the pyrazolone ring through the nitrogen atom (preferably, 5- or 6-membered heterocyclic group containing 1 to 4 nitrogen atom(s)).

In the general formula (I), the alkyl group and the alkyl moiety preferably have from 1 to 36 carbon atoms, and the aryl group and the aryl moiety preferably have from 6 to 36 carbon atoms.

Of the compounds represented by general formula (I), preferred compounds can be represented by the following general formula (Ib):

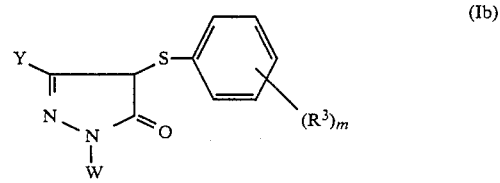

wherein W represents a phenyl group substituted with at least one halogen atom, an alkyl group, an alkoxy group, an alkoxycarbonyl group or a cyano group; $R^3$ represents a hydrogen atom, a halogen atom, an acylamino group, a sulfonamido group, a carbamoyl group, a sulfamoyl group, an alkylthio group, an alkoxycarbonyl group, a hydroxy group, an alkyl group, an alkoxy group or an aryl group; m represents an integer of from 1 to 5 and when m is 2 or more, $R^3$'s may be the same or different; and Y represents an acylamino group or an anilino group.

In the general formula (Ib), the alkyl group and the alkyl moiety preferably have from 1 to 36 carbon atoms, and the aryl group and the aryl moiety preferably have from 6 to 36 carbon atoms.

Of the compounds represented by the general formula (Ib), more preferred compounds can be represented by the following general formula (Ic):

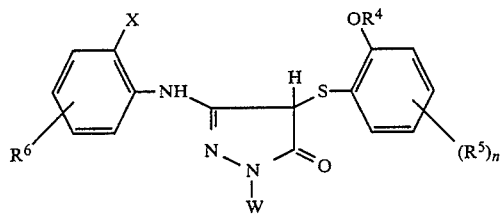

wherein W has the same meaning as defined in the general formula (Ib); $R^4$ represents an alkyl group or an aryl group; X represents a halogen atom or an alkoxy group; $R^5$ represents a hydrogen atom, a hydroxy group, a halogen atom, an alkyl group, an alkoxy group or an aryl group; $R^6$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group, or a trichloromethyl group; and n represents an integer of from 1 to 4.

In the general formula (Ic), the alkyl group and the alkyl moiety preferably have from 1 to 36 carbon atoms, and the aryl group and the aryl moiety preferably have from 6 to 36 carbon atoms.

The magenta couplers represented by general formula (Ic) are described in more detail below.

In general formula (Ic), W is a substituted phenyl group. Substituents for the phenyl group include a halogen atom (for example, a chlorine atom, a bromine atom, a fluorine atom, etc.), an alkyl group having from 1 to 22 carbon atoms (for example, a methyl group, an ethyl group, a tetradecyl group, a tert-butyl group, etc.), an alkoxy group having from 1 to 22 carbon atoms (for example, a methoxy group, an ethoxy group, an octyloxy group, a dodecyloxy group, etc.), an alkoxycarbonyl group having from 2 to 23 carbon atoms (for example, a methoxycarbonyl group, an ethoxycarbonyl group, a tetradecyloxycarbonyl group, etc.), or a cyano group.

X in the general formula (Ic) represents a halogen atom (for example, a chlorine atom, a bromine atom, a fluorine atom, etc.) or an alkoxy group having from 1 to 22 carbon atoms (for example, a methoxy group, an octyloxy group, a dodecyloxy group, etc.).

$R^6$ in the general formula (Ic) represents a hydrogen atom, a halogen atom (for example, a chlorine atom, a bromine atom, a fluorine atom, etc.), a straight chain or branched chain alkyl group (for example, a methyl group, a tert-butyl group, a tetradecyl group, etc.), an alkoxy group (for example, a methoxy group, an ethoxy group, a 2-ethylhexyloxy group, a tetradecyloxy group, etc.), an acylamino group (for example, an acetamido group, a benzamido group, a butanamido group, a tetradecanamido group, an α-(2,4-di-tert-amylphenoxy)acetamido group, an α-(2,4-di-tert-amylphenoxy)butyramido group, an α-(3-pentadecylphenoxy)hexanamido group, an α-(4-hydroxy-3-tert-butylphenoxy)tetradecanamido group, a 2-oxopyrrolidin-1-yl group, a 2-oxo-5-tetradecylpyrrolidin-1-yl group, an N-methyltetradecanamido group, etc.), a sulfonamido group (for example, a methanesulfonamido group, a benzenesulfonamido group, a p-toluene-sulfonamido group, an octanesulfonamido group, a p-dodecylbenzenesulfonamido group, an N-methyltetradecanesulfonamido group, etc.), a sulfamoyl group (for example, an N-methylsulfamoyl group, an N-hexadecylsulfamoyl group, an N-[3-(dodecyloxy)propyl]sulfamoyl group, an N-[4-(2,4-di-tert-amylphenoxy)butyl]sulfamoyl group, an N-methyl-N-tetradecylsulfamoyl group, etc.), a carbamoyl group (for example, an N-methylcarbamoyl group, an N-octadecylcarbamoyl group, an N-[4-(2,4-di-tert-amylphenoxy)butyl]carbamoyl group, an N-methyl-N-tetradecylcarbamoyl group, etc.), a diacylamino group (for example, an N-succinimido group, an N-phthalimido group, a 2,5-dioxo-1-oxazolidinyl group, a 3-dodecyl-2,5-dioxo-1-hydantoinyl group, a 3-(N-acetyl-N-dodecylamino)succinimido group, etc.), an alkoxycarbonyl group (for example, a methoxycarbonyl group, a tetradecyloxycarbonyl group, a benzyloxycarbonyl group, etc.), an alkoxysulfonyl group (for example, a methoxysulfonyl group, an octyloxysulfonyl group, a tetradecyloxysulfonyl group, etc.), an aryloxysulfonyl group (for example, a phenoxysulfonyl group, a 2,4-di-tert-amylphenoxysulfonyl group, etc.), an alkanesulfonyl group (for example, a methanesulfonyl group, an octanesulfonyl group, a 2-ethylhexanesulfonyl group, a hexadecanesulfonyl group, etc.), an arylsulfonyl group (for example, a benzenesulfonyl group, a 4-nonylbenzenesulfonyl group, etc.), an alkylthio group (for example, an ethylthio group, a hexylthio group, a benzylthio group, a tetradecylthio group, a 2-(2,4-di-tert-amylphenoxy)ethylthio group, etc.), an arylthio group (for example, a phenylthio group, a p-tolylthio group, etc.), an alkyloxycarbonylamino group (for example, an ethyloxycarbonylamino group, a benzyloxycarbonylamino group, a hexadecyloxycarbonylamino group, etc.), an alkylureido group (for example, an N-methylureido group, an N,N-dimethylureido group, an N-methyl-N-dodecylureido group, an N-hexadecylureido group, an N,N-dioctadecylureido group, etc.), an acyl group (for example, an acetyl group, a benzoyl group, an octadecanoyl group, a p-dodecanamidobenzoyl group, etc.), a nitro group, a carboxy group or a trichloromethyl group. In the above-described substituents, the alkyl moieties thereof preferably have from 1 to 36 carbon atoms, and the aryl moieties thereof preferably have from 6 to 36 carbon atoms.

$R^4$ in the general formula (Ic) represents an alkyl group having from 1 to 22 carbon atoms (for example, a methyl group, a propyl group, a butyl group, a 2-methoxyethyl group, a methoxymethyl group, a hexyl group, a 2-ethylhexyl group, a dodecyl group, a hexadecyl group, a 2-(2,4-di-tert-amylphenoxy)ethyl group, a 2-dodecyloxyethyl group, etc.) or an aryl group having from 6 to 36 carbon atoms (for example, a phenyl group, an α- or β-naphthyl group, a 4-tolyl group, etc.).

$R^5$ in the general formula (Ic) represents a hydrogen atom, a hydroxy group, an aryl group (preferably a phenyl group, a naphthyl group), or a halogen atom, an alkyl group, or an alkoxy group, each as defined for $R^6$ above [that is, a halogen atom (for example, a chlorine atom, a bromine atom, a fluorine atom, etc.), a straight chain or branched chain alkyl group (for example, a methyl group, a tert-butyl group, a tetradecyl group, etc.), an alkoxy group (for example, a methoxy group, an ethoxy group, a 2-ethylhexyloxy group, a tetradecyloxy group, etc.)].

Of the couplers represented by general formula (Ic) those in which the total number of carbon atoms included in the groups represented by $R^4$ and $R^5$ is not less than 6 are particularly preferred for achieving the objects of the present invention.

Specific examples of typical couplers according to the present invention are set forth below, but the present invention is not to be construed as being limited to these compounds.

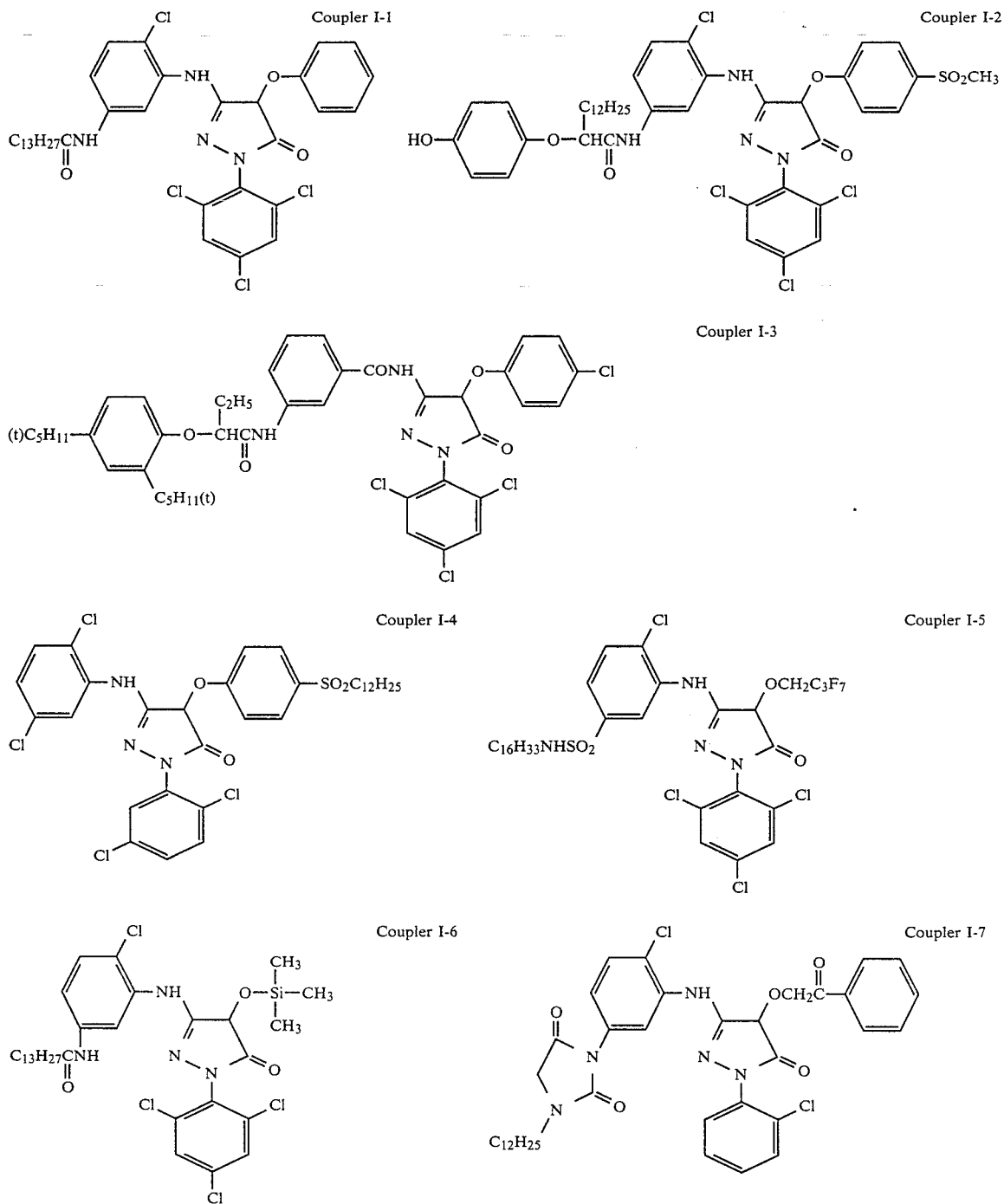

-continued
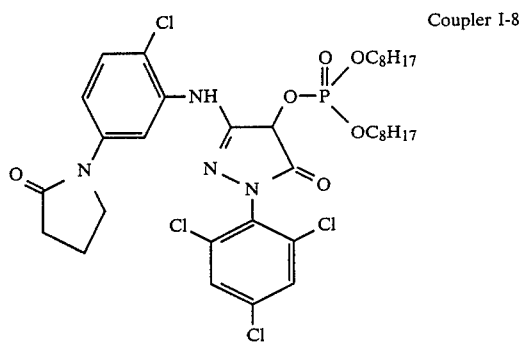
Coupler I-8
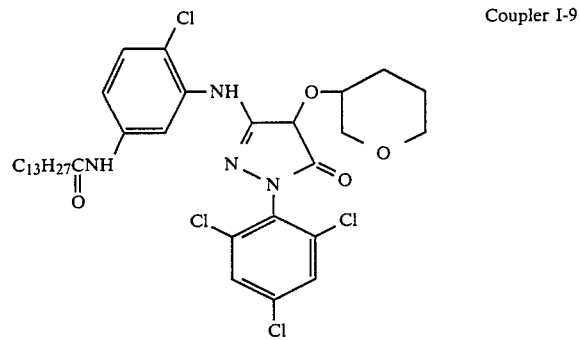
Coupler I-9
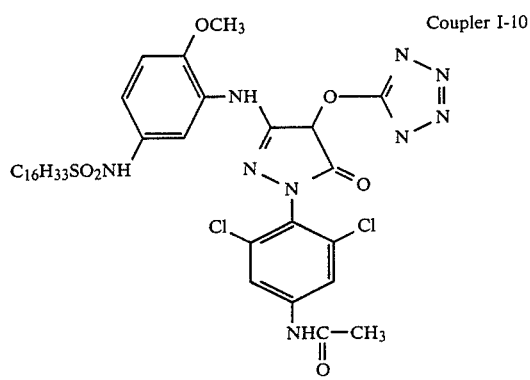
Coupler I-10
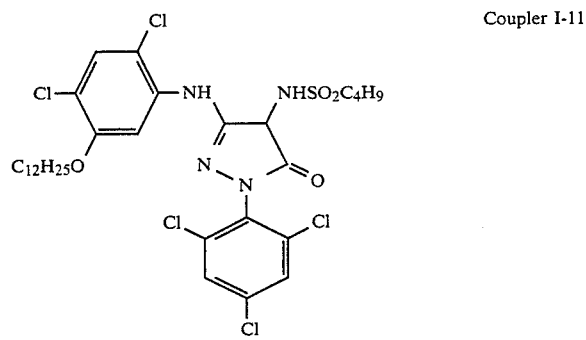
Coupler I-11
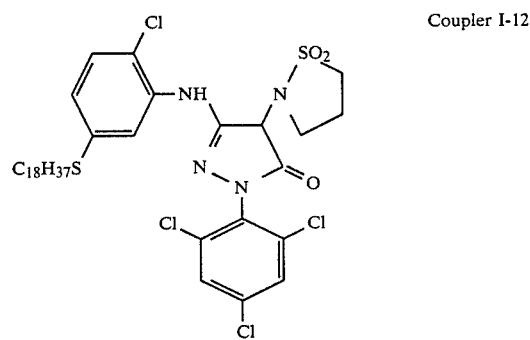
Coupler I-12
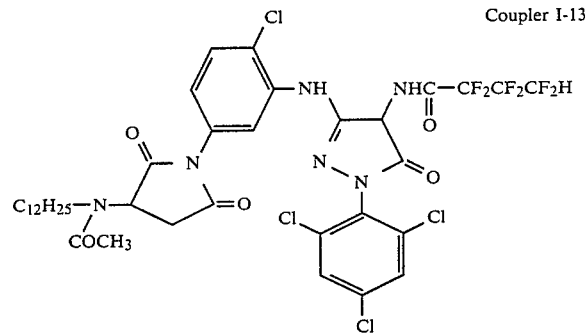
Coupler I-13
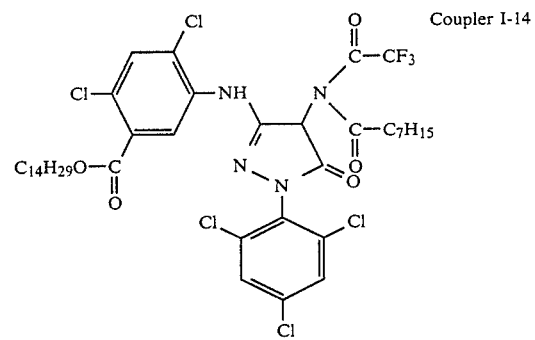
Coupler I-14
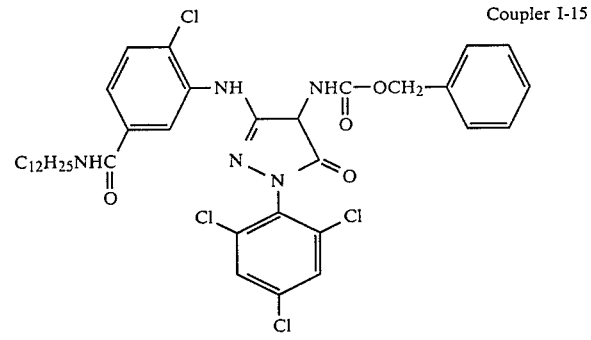
Coupler I-15

-continued
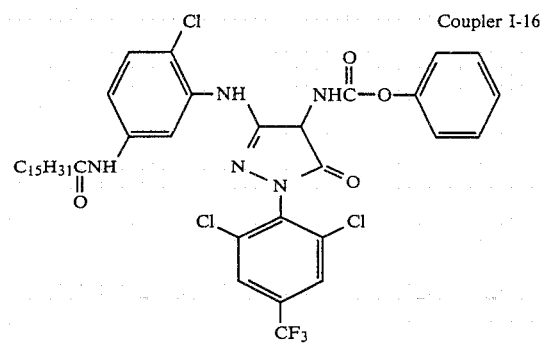
Coupler I-16
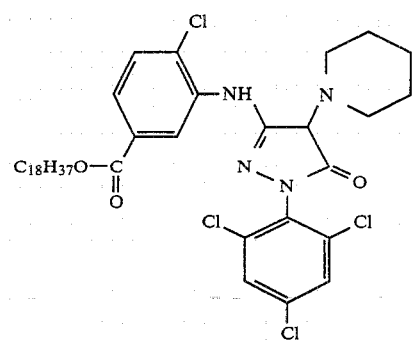
Coupler I-17
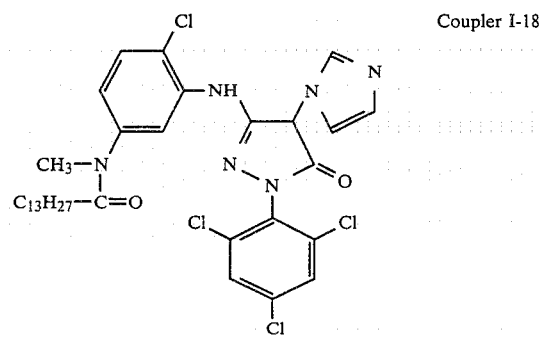
Coupler I-18
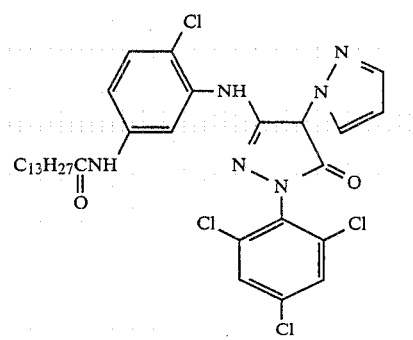
Coupler I-19
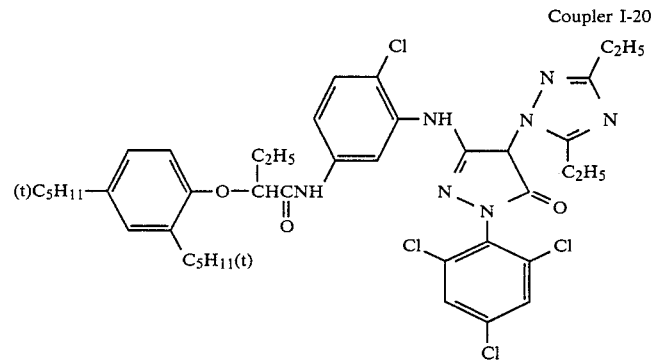
Coupler I-20
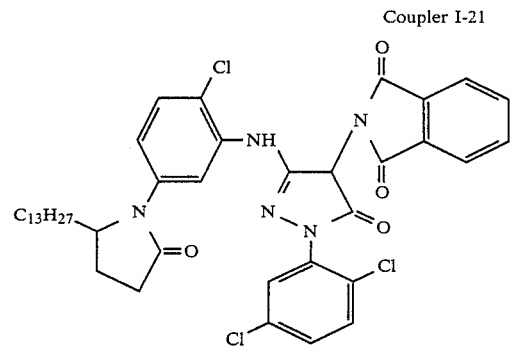
Coupler I-21
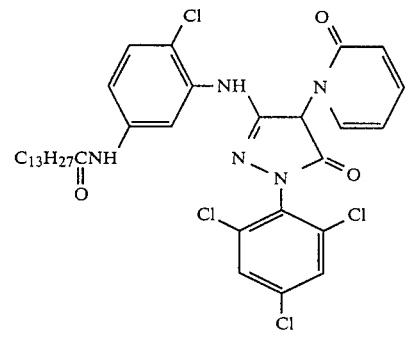
Coupler I-22
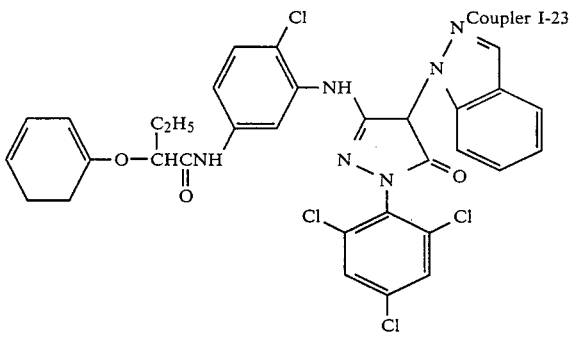
Coupler I-23

-continued
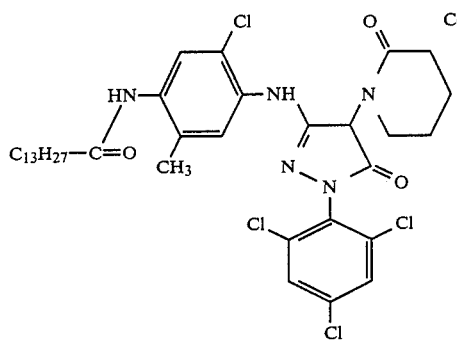
Coupler I-24
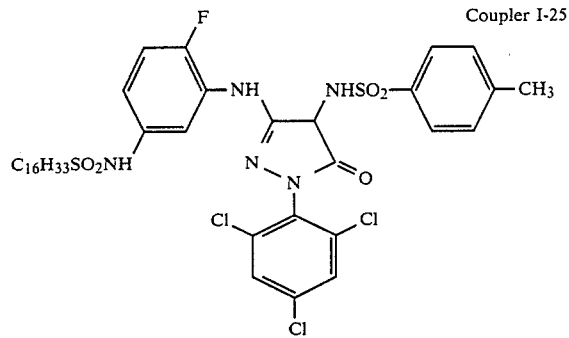
Coupler I-25
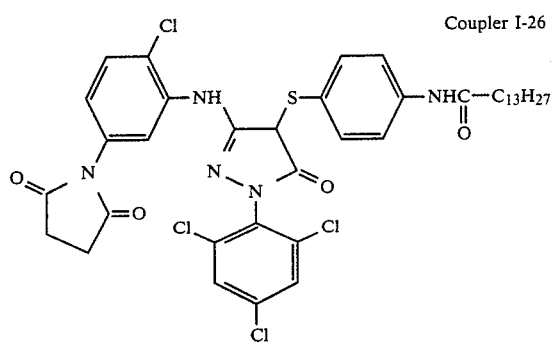
Coupler I-26
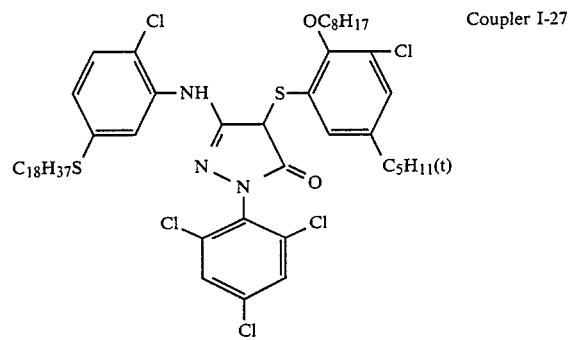
Coupler I-27
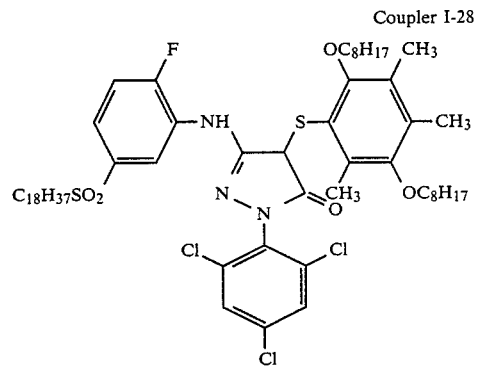
Coupler I-28
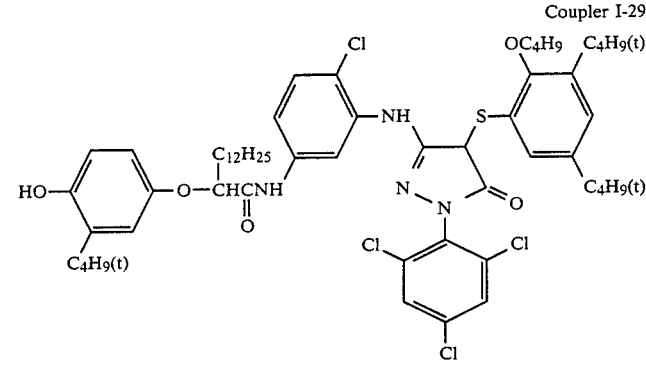
Coupler I-29
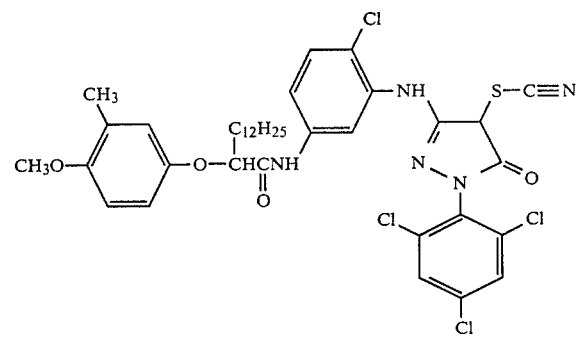
Coupler I-30

-continued
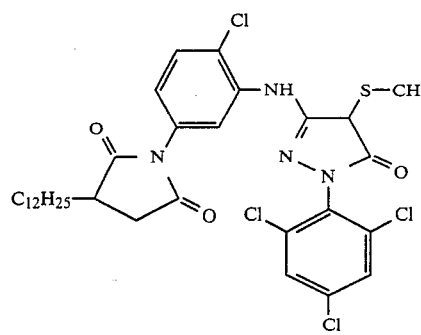
Coupler I-31
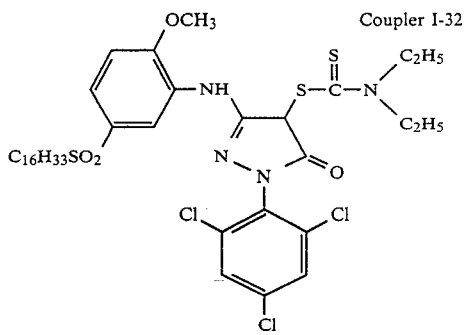
Coupler I-32
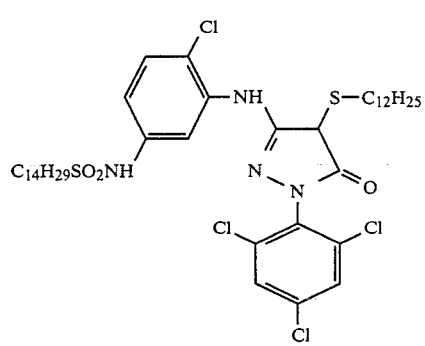
Coupler I-33
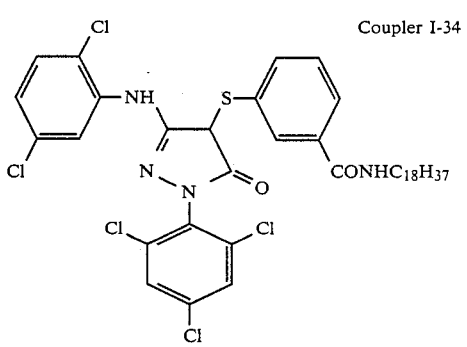
Coupler I-34
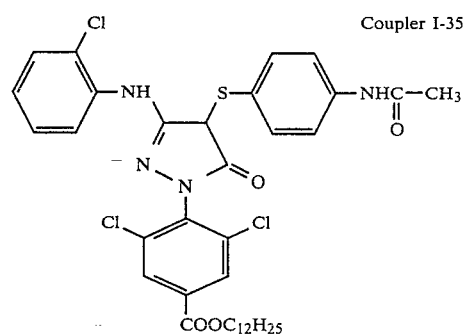
Coupler I-35
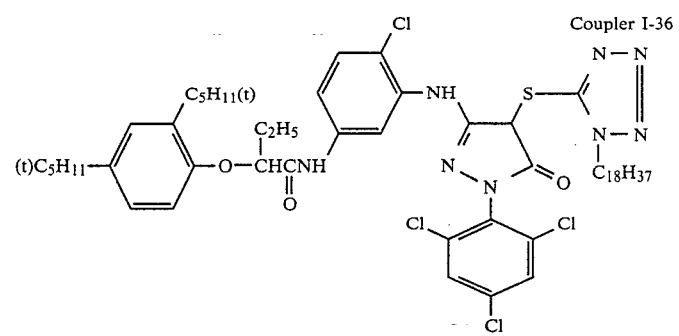
Coupler I-36
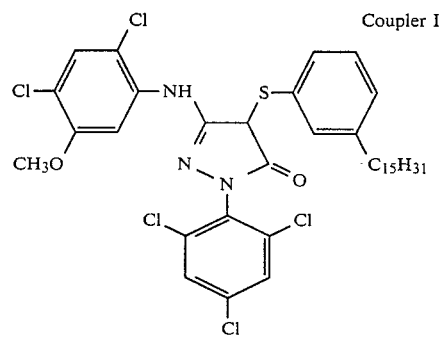
Coupler I-37
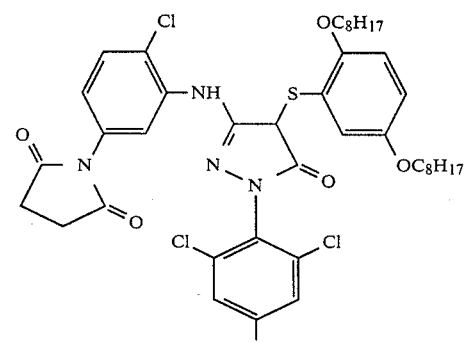
Coupler I-38

-continued
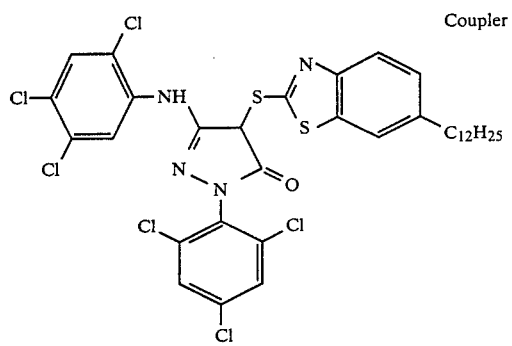
Coupler I-39
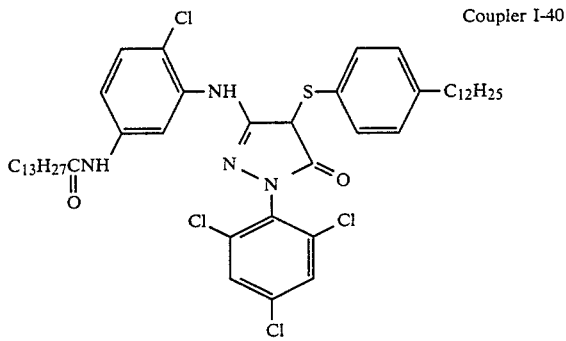
Coupler I-40
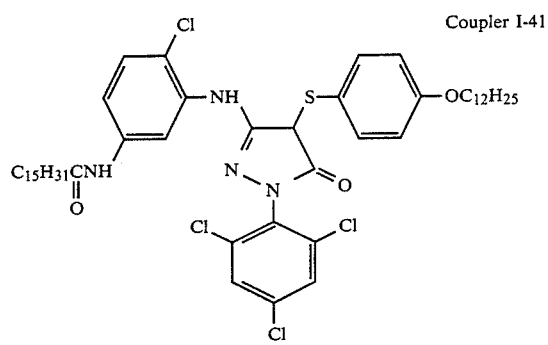
Coupler I-41
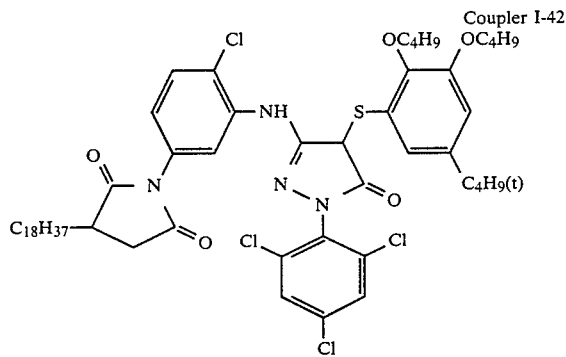
Coupler I-42
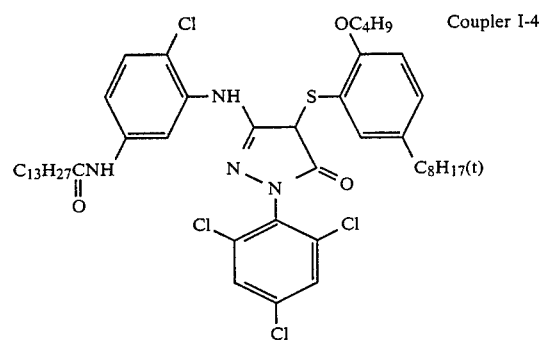
Coupler I-43
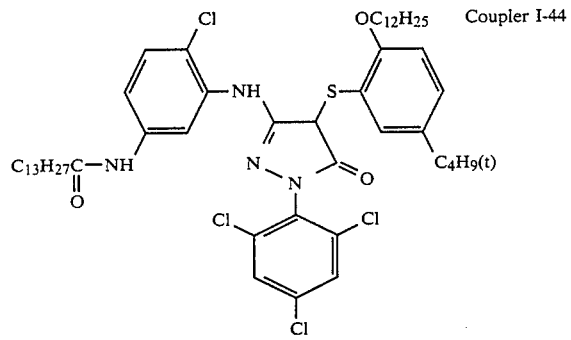
Coupler I-44
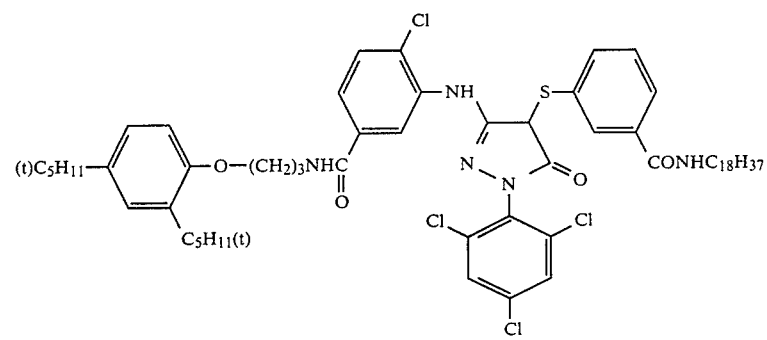
Coupler I-45

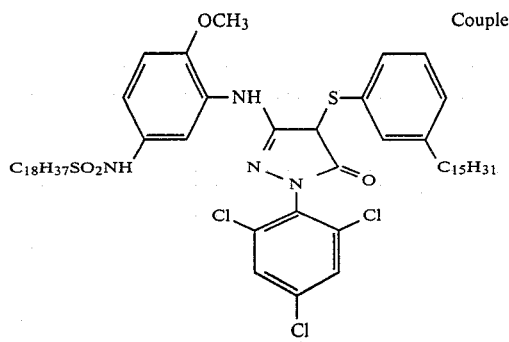

Coupler I-46

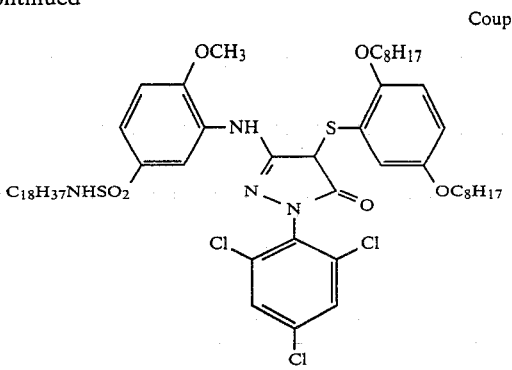

Coupler I-47

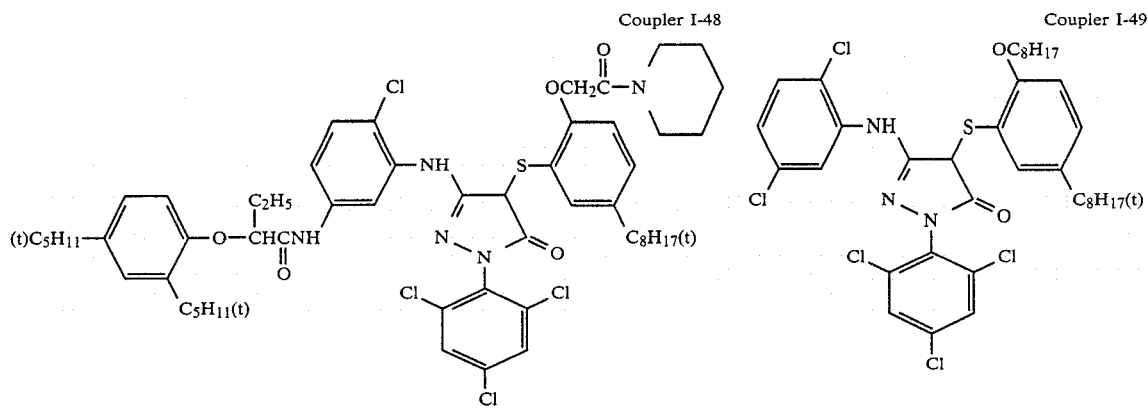

Coupler I-48              Coupler I-49

Next, the compounds represented by the general formula (II) are described:

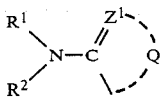  (II)

wherein $R^1$ and $R^2$, which may be the same or different, each represents a hydrogen atom, an alkyl group or an aryl group, provided that both $R^1$ and $R^2$ do not represent hydrogen atoms at the same time; $Z^1$ represents a methine group, a substituted methine group or the group —N=; and Q represents an atomic group which contains a nitrogen atom, a sulfur atom or an oxygen atom and is necessary to form a 5-membered or a 6-membered heterocyclic ring together with the group

The compounds represented by the general formula (II) are described in more detail below.

The alkyl group for $R^1$ and $R^2$ includes a straight chain or branched chain alkyl group having from 1 to 32 carbon atoms, an aralkyl group, an alkenyl group, a cycloalkyl group, a cycloalkenyl group and an alkynyl group, and each of these groups may be substituted with a halogen atom (for example, a chlorine atom, a fluorine atom, etc.), an aryl group (for example, a phenyl group, an α- or β-naphthyl group, a 2,4-dichlorophenyl group, a 3-pentadecylphenyl group, a 2,4-di-tert-amylphenyl group, etc.), a heterocyclic group (for example, a 2-pyridyl group, a 2-benzothiazolyl group, a 2-furyl group, an N-piperidyl group, an N-phthalimido group, etc.), a cyano group, an alkoxy group (for example, a methoxy group, a butoxy group, a 2-ethylhexyloxy group, a 2-methanesulfonylethoxy group, a 3-phenoxypropoxy group, a hexadecyloxy group, etc.), an aryloxy group (for example, a phenoxy group, a 4-chlorophenoxy group, a 2,4-di-tert-butylphenoxy group, a 3-methanesulfonamidophenoxy group, a 4-cyanophenoxy group, a 2-naphthoxy group, etc.), an acylamino group (for example, an acetamido group, a benzamido group, a (2,4-di-tert-amylphenoxy)acetamido group, a 2-(2-chlorophenoxy)tetradecanamido group, a 3-[2-(2,4-di-tert-amylphenoxy)butyramido]benzamido group, etc.), an imido group (for example, a succinimido group, a phthalimido group, an N-hydantoinyl group, etc.), an anilino group (for example, a phenylamino group, a 2-chloroanilino group, an N-methylanilino group, a 2-chloro-5-tetradecanamidoanilino group, a 4-methoxyanilino group, etc.), an alkylamino group (for example, a methylamino group, an N,N-diethylamino group, an N-(2-ethoxyethyl)amino group, etc.), a heterocyclic amino group (for example, a 2-pyridylamino group, a 2-imidazolylamino group, a 2-pyrimidylamino group, etc.), a ureido group (for example, a methylureido group, an N,N-dipropylureido group, a phenylureido group, a 4-chlorophenylureido group, a 4-propanesulfonylphenylureido group, etc.), a sulfamoylamino group (for example, an N,N-dimethylsulfamoylamino group, an N-methyl-N-phenylsulfamoylamino group, an N,N-diisopropylsulfamoylamino group, etc.), an alkylthio group (for example, a butylthio group, a dodecylthio group, a 3-phenoxypropylthio group, a cyclopentylthio group, a benzylthio group, etc.), an arylthio group (for example, a phenylthio group, a 2-methylphenylthio group, a 4- dodecylphenylthio group, a 2-butyloxy-5-tert-octylphenylthio group, a 4-dodecyloxyphenylthio group, etc.), a heterocyclic thio group (for example, a 2-benzoxazolylthio group, a 1-ethyltetrazole-5-thio group, an

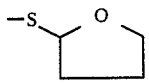

group, etc.), an alkoxycarbonylamino group (for example, a methoxycarbonylamino group, a butoxycarbonylamino group, etc.), an aryloxycarbonylamino group (for example, a phenoxycarbonylamino group, etc.), a sulfonamido group (for example, a methane-sulfonamido group, a benzenesulfonamido group, a dodecane-sulfonamido group, a 4-dodecyloxybenzenesulfonamido group, etc.), a carbamoyl group (for example, an N-methylcarbamoyl group, an N,N-dibutylcarbamoyl group, an N-phenylcarbamoyl group, an N-methyl-N-phenylcarbamoyl group, etc.), a sulfamoyl group (for example, an N-butylsulfamoyl group, an N-phenylsulfamoyl group, an N,N-dipropylsulfamoyl group, an N-methyl-N-phenylsulfamoyl group, etc.), a sulfonyl group (for example, a methanesulfonyl group, a dodecanesulfonyl group, a benzenesulfonyl group, a 4-toluenesulfonyl group, etc.), a sulfinyl group (for example, a methanesulfinyl group, a benzenesulfinyl group, etc.), an acyl group (for example, an acetyl group, a propanoyl group, a dodecanoyl group, a benzoyl group, a pivaloyl group, a 4-methoxybenzoyl group, etc.), an alkoxycarbonyl group (for example, a methoxycarbonyl group, a tetradecyloxycarbonyl group, etc.), an aryloxycarbonyl group (for example, a phenoxycarbonyl group, etc.), a phosphonyl group (for example, a methoxyphosphonyl group, a butylphosphonyl group, a phenylphosphonyl group, etc.), an imino group (for example, a propylideneimino group, etc.), a cyanothio group, an acyloxy group (for example, an acetoxy group, an octanoyloxy group, a benzoyloxy group, etc.), a carbamoyloxy group (for example, an N-acetylaminooxy group, an N-benzoylaminooxy group, etc.), a silyloxy group (for example, a trimethylsilyloxy group, a dibutylmethylsilyloxy group, etc.), a sulfonyloxy group (for example, a methanesulfonyloxy group, a benzenesulfonyloxy group, etc.), a heterocyclic oxy group (for example, a 1-phenyltetrazol-5-oxy group, a 2-tetrahydropyranyloxy group, etc.), a hydroxy group, or a nitro group.

The aryl group for $R^1$ and $R^2$ is preferably an aryl group having from 6 to 38 carbon atoms including a phenyl group, an α- or β-naphthyl group, a phenyl group substituted with a substituent as defined for the above-described alkyl group for $R^1$ and $R^2$, and an α- or β-naphthyl group substituted with a substituent as defined for the above-described alkyl group for $R^1$ and $R^2$.

$Z^1$ represents a methine group; a substituted methine group including, as a substituent, an alkyl group or an aryl group each of which has the same meaning as defined for $R^1$ or $R^2$, a halogen atom (for example, a chlorine atom, a bromine atom, etc.), an alkoxy group (for example, a methoxy group, a butoxy group, etc.), an acylamino group (for example, an acetamido group, a benzamido group, a (2,4-di-tert-amylphenoxy)acetamido group, etc.), an imido group (for example, an N-succinimido group, an N-phthalimido group, etc.), a sulfonamido group (for example, a methanesulfonamido group, a benzenesulfonamido group, etc.), a carbamoyl group (for example, an N-methylcarbamoyl group, an N-phenylcarbamoyl group, an N,N-dipropylcarbamoyl group, etc.), a sulfamoyl group (for example, an N-butylsulfamoyl group, an N,N-dipropylsulfamoyl group, an N-methyl-N-phenylsulfamoyl group, etc.), an alkoxycarbonyl group (for example, a methoxycarbonyl group, a tetradecyloxycarbonyl group, etc.), an alkylsulfonyl group (for example, a methanesulfonyl group, a dodecanesulfonyl group, etc.), an alkylthio group (for example, an octylthio group, a 3-phenoxypropylthio group, etc.), a hydroxy group, etc.; or the group —N=.

Q represents an atomic group which contains a nitrogen atom, a sulfur atom or an oxygen atom and is necessary to form a 5membered or 6membered heterocyclic ring together with the group of

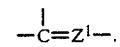

Of the compounds represented by general formula (II), preferred heterocyclic amino compounds can be represented by the following general formula (III):

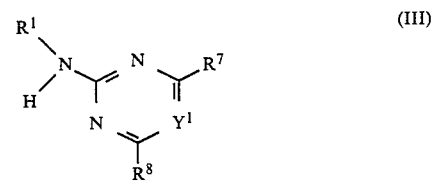

(III)

wherein $R^1$ has the same meaning as defined above; $R^7$ and $R^8$ each represents a hydrogen atom, an alkyl group or an aryl group each of which has the same meaning as defined for $R^1$ or $R^2$ above, or a halogen atom, a heterocyclic group, a cyano group, an alkoxy group, an aryloxy group, an acylamino group, a heterocyclic oxy group, an imido group, an anilino group, an alkylamino group, a heterocyclic amino group, a ureido group, a sulfamoylamino group, an alkylthio group, an arylthio group, a heterocyclic thio group, an alkoxycarbonylamino group, an aryloxycarbonylamino group, a sulfonamido group, a carbamoyl group, a sulfamoyl group, a sulfonyl group, a sulfinyl group, an acyl group, an alkoxycarbonyl group, an aryloxycarbonyl group, a phosphonyl group, an imino group, a cyanothio group, an acyloxy group, a carbamoyloxy group, a hydroxy group, a silyloxy group, a sulfonyloxy group or a nitro group each of which has the same meaning as defined for the substituent for the alkyl group of $R^1$ above; and $Y^1$ represents a methine group, the group

where $R^7$ is as above defined, or the group —N=.

More preferred heterocyclic amino compounds used in the present invention can be represented by the following general formula (IV):

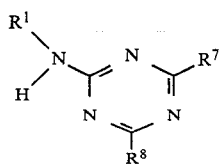

(IV)

wherein $R^1$, $R^7$ and $R^8$ each has the same meaning as defined above.

Still further preferred heterocyclic amino compounds used in the present invention can be represented by the following general formula (V):

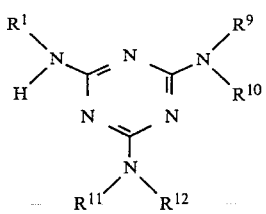

(V)

wherein $R^1$ has the same meaning as defined above; and $R^9$, $R^{10}$, $R^{11}$ and $R^{12}$ each has the same meaning as defined for $R^1$ or $R^2$ above.

Specific examples of the heterocyclic amino compounds according to the present invention are set forth below, but the present invention is not to be construed as being limited th these compounds.

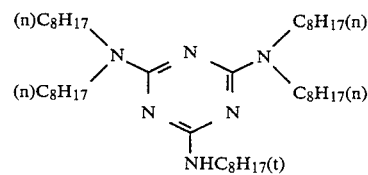

Compound 1

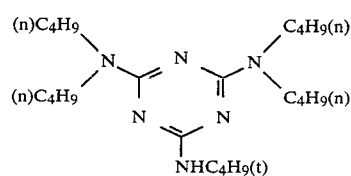

Compound 2

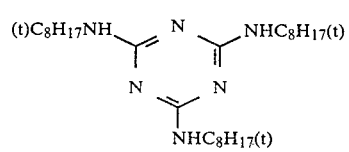

Compound 3

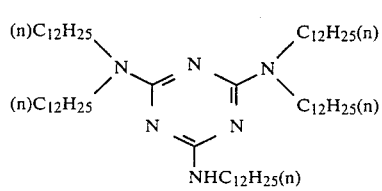

Compound 4

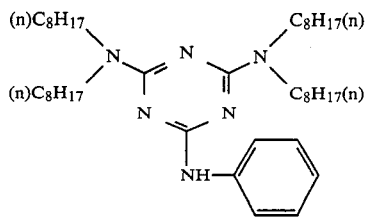

Compound 5

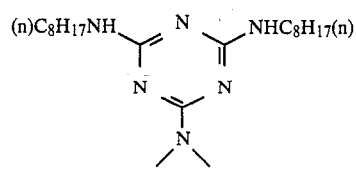

Compound 6

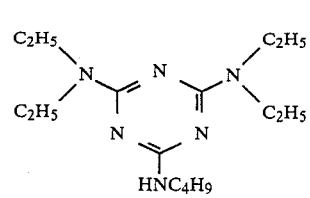

Compound 7

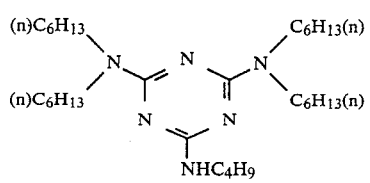

Compound 8

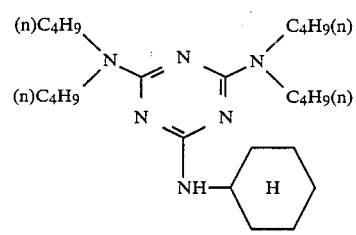

Compound 9

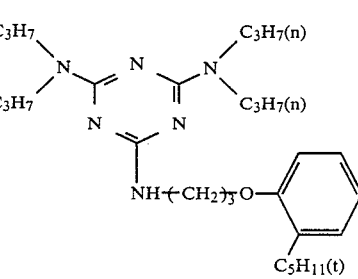

Compound 10

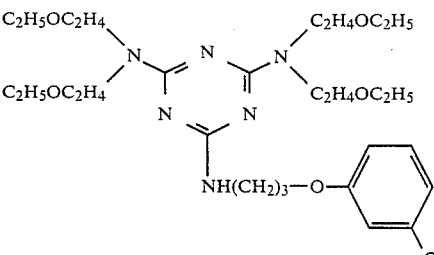

Compound 11

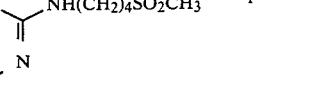 Compound 12

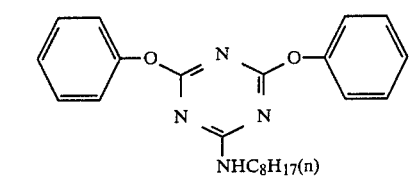 Compound 13

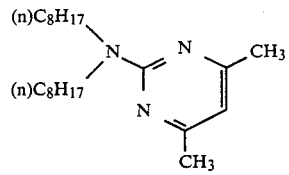 Compound 14

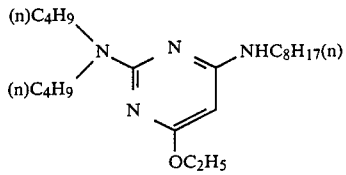 Compound 15

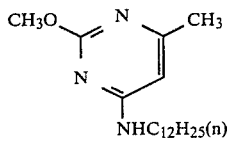 Compound 16

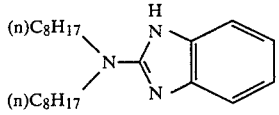 Compound 17

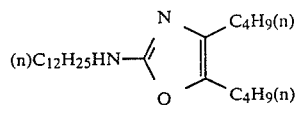 Compound 18

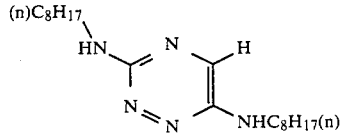 Compound 19

Compound 20

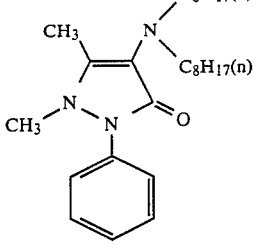 Compound 21

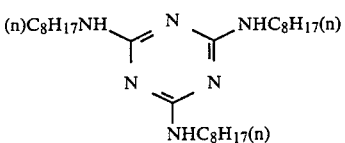 Compound 22

These compounds can be synthesized by the method as described in *J. Amer. Chem. Soc.*, Vol. 73, pages 2981 and 2984 (1951). Also, compounds other than triazine derivatives can be synthesized in a similar manner.

Typical synthesis examples of the heterocyclic amino compounds according to the present invention are illustrated below.

SYNTHESIS EXAMPLE 1

Synthesis of Compound 6

Step 1: Synthesis of 2,6-di-n-octylamino-4-chloro-1,3,5-triazine (Intermediate A)

37 g (0.2 mol) of cyanuric chloride was dissolved in 80 ml of hot acetone and the solution was rapidly added to 120 ml of ice water (crushed ice:water=1:1) with vigorous stirring. The temperature reached 0° to 5° C. 56.8 g (0.44 mol) of n-octylamine was gradually added dropwise while maintaining the temperature at 10° C. or below. Then, the temperature was raised to 40° C. by heating and the mixture was heated on a water bath for 1 hour. Since the pH of the reaction solution turned into the acid region (pH<2), granules of potassium hydroxide was gradually added to maintain the pH around neutral (the time required was 1 hour). The product deposited in the reaction solution was cooled and separated by filtration. The crystals were thoroughly washed with water and dried. The crude crystals were recrystallized from ethanol to obtain 48 g of Intermediate A having a melting point of 171°–172° C.

Step 2: Synthesis of Compound 6

37 g (0.1 mol) of Intermediate A obtained in Step 1 above, 26 g (0.11 mol) of di-n-octylamine and 14 g (0.11 mol) of anhydrous potassium carbonate were added to 200 ml of dioxane and the mixture was refluxed by heating on a steam bath for 1 hour. Then, 5.2 g of di-n-octylamine and 7 g of anhydrous potassium carbonate were added and the system further refluxed by heating for 1 hour. After cooling, the solid (inorganic compound) deposited was removed by filtration, and to the filtrate was added 500 ml of ethyl acetate and the system washed with a saturated aqueous sodium chloride solution. The resulting ethyl acetate layer was thoroughly dried with anhydrous sodium sulfate and the solvent was distilled off under reduced pressure. The residue was crystallized with ethanol to obtain 39 g of Compound 6 as white crystals having a melting point of 48.5° to 49.5° C.

Elemental Analysis: Calculated (%): H: 12.27, C: 73.11, N: 14.62. Found (%): H: 12.25, C: 73.15, N: 14.66.

SYNTHESIS EXAMPLE 2

Synthesis of Compound 22

37 g (0.1 mol) of Intermediate A obtained in Step 1 of Synthesis Example 1, 14.2 g (0.11 mol) of n-octylamine and 14 g (0.11 mol) of anhydrous potassium carbonate were added to 200 ml of dioxane and the mixture was refluxed by heating with stirring. Then, the same procedure as described in Synthesis Example 1 was conducted and following crystallization with ethanol there was obtained 28.2 g of Compound 22 having a melting point of 40° to 42° C.

Elemental Analysis: Calculated (%): H: 11.76, C: 70.07, N: 18.16. Found (%): H: 11.77, C: 70.13; N: 18.13.

SYNTHESIS EXAMPLES 3 TO 6

The following compounds were synthesized in the same manner as described in Synthesis Examples 1 and 2.

| Compound | Melting Point or Boiling Point | Elemental Analysis (upper: calculated, lower: found) | | |
|---|---|---|---|---|
| | | H (%) | C (%) | N (%) |
| 1 | Oily product which could not be subjected to vacuum distillation and was purified by a column | 12.62<br>12.58 | 75.15<br>75.20 | 12.23<br>12.22 |
| 2 | Boiling Point: 176–180° C. at 0.35 mmHg | 11.40<br>11.41 | 67.93<br>67.96 | 20.67<br>20.65 |
| 3 | Melting Point: 147–148° C. | 11.76<br>11.74 | 70.07<br>70.10 | 18.16<br>18.13 |
| 21 | Oily product which was purified by a column (decomposed by vacuum distillation; boiling point: 180–2000° C. at 0.5 mmHg) | 10.61<br>10.63 | 75.83<br>75.82 | 9.83<br>9.89 |

An amount of the compound represented by general formula (II), (III), (IV) or (V) is preferably from 0.05 mol to 5 mols and more preferably from 0.50 mol to 3 mols per mol of the 2-equivalent magenta coupler represented by general formula (I), (Ib) or (Ic).

The compound represented by general formula (I), (Ib) or (Ic) and the compound represented by general formula (II), (III), (IV) or (V) can be used by dissolving the same in a solvent having a high boiling point as described hereinafter and then dispersing the solution. [That is, the 2-equivalent magenta coupler represented by general formula (I), (Ib) or (Ic) and the compound represented by general formula (II), (III), (IV) or (V) are present in a droplet of an organic solvent having a boiling point of not less than 180° C. dispersed in a hydrophilic colloid.] Also, they may be used by directly dissolving the compound represented by general formula (I), (Ib) or (Ic) in the compound represented by general formula (II), (III), (IV) or (V).

Any known solvents can be used as the above-described solvent having a high boiling point, particularly an organic solvent having a boiling point of not less than 180° C. For example, a phthalic acid alkyl ester (e.g., dibutyl phthalate, dioctyl phthalate, etc.), a phosphoric acid ester (e.g., diphenyl phosphate, triphenyl phosphate, tricresyl phosphate, dioctylbutyl phosphate, etc.), a citric acid ester (e.g., tributyl acetylcitrate, etc.), a benzoic acid ester (e.g., octyl benzoate, etc.), an alkylamide (e.g., diethyl laurylamide, etc.), a fatty acid ester (e.g., dibutoxyethyl succinate, dioctyl azelate, etc.), a trimesic acid ester (e.g., tributyl trimesate, etc.), etc., as described in U.S. Pat. No. 2,322,027 is preferably used. In particular, an alkyl phosphate (e.g., diphenyl phosphate, triphenyl phosphate, tricresyl phosphate, dioctyl butyl phosphate, etc.) is preferred.

Oil-soluble couplers are preferably used in the present invention.

Examples of useful conventional magenta couplers, which can be used together with the 2-equivalent magenta coupler of the 5-pyrazolone type according to the present invention, include a pyrazolotriazole type coupler and an imidazopyrazole type coupler. Examples of yellow couplers include a benzoylacetanilide type compound and a pivaloylacetanilide type compound which have been found to be advantageously used in the practice of the present invention. Examples of useful cyan couplers include a phenol type compound and a naphthol type compound.

In addition, colored couplers, DIR couplers, and compounds which release a development inhibitor as development may be used together.

Two or more of the above-described couplers may be contained in the same layer. Two or more layers may also contain the same compound.

These couplers are generally added in an amount of from $2 \times 10^{-3}$ mol to $5 \times 10^{-1}$ mol, preferably from $1 \times 10^{-2}$ mol to $5 \times 10^{-1}$ mol, per mol of silver in the emulsion layer.

The mole ratio of the high boiling point solvent/coupler is preferably from 0.0 to 2.0.

In order to incorporate the above-described couplers into a hydrophilic colloid layer, the method using the above-described organic solvent having a high boiling point as described in U.S. Pat. No. 2,322,027 can be employed, or they may be dissolved in an organic solvent having a boiling point of from about 30° to 150° C., for example, a lower alkyl acetate (e.g., ethyl acetate, butyl acetate, etc.), ethyl propionate, sec-butyl alcohol, methyl isobutyl ketone, β-ethoxyethyl acetate, methyl cellosolve acetate, etc., and then the solution dispersed in a hydrophilic colloid. The above-described organic solvents having a high boiling point and the above-described organic solvents having a low boiling point may be used as mixtures, if desired.

Furthermore, the dispersing method using a polymeric material as described in Japanese Patent Publication No. 39853/76, Japanese Patent Application (OPI) No. 59943/76 and also be used.

When a coupler having an acid group, such as a carboxylic acid group, a sulfonic acid group, etc., is used, it can be incorporated in a hydrophilic colloid as an alkaline aqueous solution thereof.

A conventional subbing layer may be used per the present invention. The subbing layer for the photographic light-sensitive material of the present invention is a hydrophilic colloid layer comprising a hydrophilic polymer such as gelatin (a binder or a protective colloid for a photographic emulsion described hereinafter can also be used) and is usually provided by coating the same on a support. By the provision of the subbing layer, in general, adhesion to the photographic emulsion layer can be improved and halation may be prevented.

The color photographic light-sensitive material of the present invention can be applied in any known color photographic light-sensitive material so long as they are subjected to color development processing, for example, color papers, color negative films, color reversal films, etc. It is particularly preferred for use in photographic light-sensitive materials for printing (for example, color papers, etc.).

The silver halide photographic emulsion used in the present invention can be prepared by using processes described in P. Glafkides, *Chimie et Physique Photographique* (published by Paul Montel Co., 1967); G. F. Duffin, *Photographic Emulsion Chemistry* (published by the Focal Press, 1966); V. L. Zelikman et al., *Making and Coating Photographic Emulsion* (published by The Focal Press, 1964); etc. Any of an acid process, neutral process or ammonia process may be used. Further, a single jet process, a double jet process, or a combination thereof can be used for reacting a soluble silver salt with a soluble halide.

A process for forming particles in the presence of excess silver ion (the so-called reverse mixing process) can also be used. One useful double jet process involves keeping the liquid phase for forming silver halide at a definite pAg, namely, the so-called controlled double jet process. According to this process, a silver halide emulsion having a regular crystal form and a nearly uniform particle size can be obtained.

Two or more silver halide emulsions prepared separately may also be blended.

In the photographic emulsion layer of the photographic light-sensitive material of the present invention, any of silver bromide, silver iodobromide, silver iodochlorobromide, silver chlorobromide and silver chloride can be used as the silver halide.

In the step of formation of silver halide particles or the step of physical ripening, a cadmium salt, a zinc salt, a lead salt, a thallium salt, an iridium salt or a complex salt thereof, a rhodium salt or a complex salt thereof, an iron salt or a complex salt thereof, etc., may be added thereto.

The photographic emulsion used in the present invention may be spectrally sensitized by methine dyes or others. Examples of dyes used include a cyanine dye, a merocyanine dye, a complex cyanine dye, a complex merocyanine dye, a holopolar cyanine dye, a hemicyanine dye, a styryl dye and a hemioxonol dye. Particularly useful dyes can be selected from the group consisting of a cyanine dye, a merocyanine dye, and a complex merocyanine dye. In these dyes, it is possible to utilize any basic heterocyclic nucleus conventionally utilized for a cyanine dye. Namely, it is possible to utilize a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus and a pyridine nucleus; the above described nuclei to which an alicyclic hydrocarbon ring is fused; and the above described nuclei to which an aromatic hydrocarbon ring is fused, namely, an indolenine nucleus, a benzindolenine nucleus, an indole nucleus, a benzoxazole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc. These nuclei may have substituents on the carbon atoms thereof.

In the merocyanine dye and the complex merocyanine dye, it is possible to utilize, as a nucleus having a ketomethylene structure, a 5- to 6-membered heterocyclic nucleus such as a pyrazolin-5-one nucleus, a thiohydantoin nucleus, a 2-thiooxazolidin-2,4-dione nucleus, a thiazolidine-2,4-dione nucleus, a rhodanine nucleus, a thiobarbituric acid nucleus, etc.

These sensitizing dyes may be used alone or a combination of them may be used. A combination of the sensitizing dyes is frequently used for the purpose of supersensitization. Examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. No. 1,344,281 and 1,507,803, Japanese Patent Publication Nos. 4936/68 and 12375/78, Japanese Patent Application (OPI) Nos. 110618/77 and 109925/77, etc.

The emulsion may contain a dye which does not have a spectral sensitization function, or a substance which does not substantially absorb visible rays and shows supersensitization together with the sensitizing dye. For example, the emulsion may contain an aminostilbene compound substituted with a nitrogen-containing heterocyclic group (for example, those described in U.S. Pat. Nos. 2,933,390 and 3,635,721), an aromatic organic acid-formaldehyde condensed product (for example, those described in U.S. Pat. No. 3,743,510), a cadmium salt, an azaindene compound, etc. Combinations as described in U.S. Pat. Nos. 3,615,613, 3,615,641, 3,617,295 and 3,635,721 are particularly useful.

The binder or protective colloid for the photographic emulsion is preferably gelatin, but other hydrophilic colloids may be used, too.

For example, it is possible to use a protein such as a gelatin derivative, a graft polymer of gelatin with other polymers, albumin, or casein; saccharides, including a cellulose compound such as hydroxyethyl cellulose, carboxymethyl cellulose, cellulose sulfate, etc., sodium alginate, a starch derivative, etc.; and synthetic hydrophilic polymeric substances such as a homopolymer or a copolymer such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc.

The gelatin may be not only lime-processed gelatin, but also acid-processed gelatin, and enzyme-processed gelatin, as described in *Bull. Soc. Sci. Phot. Japan*, No. 16, page 30 (1966).

The present invention can be applied to a multilayer multicolor photographic light-sensitive material comprising at least two layers having different spectral sensitivities on a support. The multilayer natural color photographic light-sensitive material generally has at least one red-sensitive emulsion layer, at least one green-sensitive emulsion layer and at least one blue-sensitive emulsion layer on the support. The order of these layers may be suitably varied as occasion demands. Generally, the red-sensitive emulsion layer contains a cyan forming coupler, the green-sensitive emulsion layer contains a magenta forming coupler, and the blue-sensitive emulsion layer contains a yellow forming coupler. However, if desired, other combinations may be utilized.

In the photographic light-sensitive material produced according to the present invention, the hydrophilic colloid layer may contain a water-soluble dye as a filter dye or for other purposes such as prevention of irradiation. Examples of such dyes include an oxonol dye, a hemioxonol dye, a styryl dye, a merocyanine dye, a cyanine dye, and an azo dye. Among them, an oxonol dye, a hemioxonol dye and a merocyanine dye are particularly useful.

In carrying out the present invention, known agents for preventing color fading may be used. Further, such dye image stabilizers in the present invention may be used alone, or two or more of them may be used together. Examples of known agents for preventing color fading include a hydroquinone derivative, a gallic acid derivative, a p-alkoxyphenol, a p-oxyphenol, a bisphenol, etc.

The photographic light-sensitive material prepared according to the present invention can also contain, as a color fog preventing agent, a hydroquinone derivative, an aminophenol derivative, a gallic acid derivative, an ascorbic acid derivative, etc.

In the photographic light-sensitive material prepared according to the present invention, it is preferred that the hydrophilic colloid layer contain an ultraviolet ray absorbing agent. For example, it is possible to use a benzotriazole compound substituted with an aryl group (for example, those described in U.S. Pat. No. 3,533,794), a 4-thiazolidone compound (for example, those described in U.S. Pat. Nos. 3,314,794 and 3,352,681), a benzophenone compound (for example, those described in Japanese Patent Application (OPI) No. 2784/71), a cinnamic acid ester compound (for example, those described in U.S. Pat. Nos. 3,705,805 and 3,707,375), a butadiene compound (for example, those described in U.S. Pat. No. 4,045,229), and a benzoxazole compound (for example, those described in U.S. Pat. No. 3,700,455). Further, it is possible to use those described in U.S. Pat. No. 3,499,762 and Japanese Patent Application (OPI) No. 48535/79. A coupler having an ultraviolet ray absorbing property (for example, an α-naphthol type cyan dye forming coupler) and a polymer having an ultraviolet ray absorbing property may also be used. These ultraviolet ray absorbing agents may be mordanted on a specified layer, if desired.

In the photographic light-sensitive material prepared according to the present invention, the photographic emulsion layer and other hydrophilic colloid layers may contain a whitening agent such as a stilbene, triazine, oxazole or coumarin compound. They may be water-soluble. Further, a water-insoluble whitening agent may be used in the form of a dispersion.

In the photographic light-sensitive material of the present invention, the photographic emulsion layer and other hydrophilic layers can be coated on a support or other layers using various known coating methods. A dip coating method, a roller coating method, a curtain coating method, an extrusion coating method, etc., can be employed for coating.

The photographic processing of the photographic light-sensitive material of the present invention can be carried out by any known process. Known processing solutions can be used. The processing temperature is selected, generally, from 18° C. to 50° C., but a temperature of lower than 18° C. or higher than 50° C. may be used. Any color development processings as far as they provide dye images can be employed depending on the purpose.

The color developing solution is generally composed of an alkaline aqueous solution containing a color developing agent. The color developing agent may be a known primary aromatic amine developing agent. Examples of these agents include a phenylenediamine (for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, 4-amino-3-methyl-N-ethyl-N-β-methoxyethylaniline, etc.).

In addition, those described in L. F. A. Mason, *Photographic Processing Chemistry* (Focal Press, 1966) pages 226 to 229, U.S. Pat. Nos. 2,193,015 and 2,592,364, Japanese Patent Application (OPI) No. 64933/73, etc., may be used.

The color developing solution may contain a pH buffer agent such as a sulfite, a carbonate, a borate or a phosphate of an alkali metal, and a development restrainer or an antifogging agent such as a bromide, an iodide, an organic antifogging agent, etc. If necessary, it may contain a water softener, a preservative such as hydroxylamine, an organic solvent such as benzyl alcohol or diethylene glycol, a development accelerator such as polyethylene glycol, a quaternary ammonium salt or an amine, a dye forming coupler, a competing coupler, a fogging agent such as sodium borohydride, a viscosity imparting agent, a polycarboxylic acid type chelating agent as described in U.S. Pat. No. 4,083,723, and an antioxidant as described in West German Patent Application (OLS) No. 2,622,950, etc.

After carrying out the color development, the photographic emulsion layers are generally subjected to bleaching. The bleaching may be carried out simultaneously with fixing or may be carried out separately. The bleaching agent may be a compound of a polyvalent metal such as iron (III), cobalt (III), chromium (VI) or copper (II), etc., a peracid, a quinone or a nitroso compound. For example, it is possible to use a ferricyanide, a bichromate, and an organic complex salt of iron (III) or cobalt (III), for example, a complex salt of an aminopolycarboxylic acid such as ethylenediaminetetraacetic acid, nitrilotriacetic acid or 1,3-diamino-2-propanol tetraacetic acid, etc., or an organic acid such as citric acid, tartaric acid, malic acid, etc.; a persulfate; a permanganate; nitrosophenol; etc. Among them, potassium ferricyanide, (ethylenediaminetetraacetato)iron (III) sodium complex and (ethylenediaminetetraacetato)iron (III) ammonium complex are particularly useful. (Ethylenediaminetetraacetato)iron (III) complexes are useful for both a bleaching solution and a mono-bath bleach-fix solution.

To the bleaching solution or the bleach-fix solution, it is possible to add a bleaching accelerator, a thiol compound, and various other additives.

In order to accelerate color development, a color developing agent or a derivative thereof may be previously incorporated into the photographic light-sensitive material. For example, it may be incorporated as a metal salt or a Schiff's base. Specific examples of these compounds which can be used are described in U.S. Pat. Nos. 3,719,492 and 3,342,559, *Research Disclosure*, No. 15159 (1976). Further, a developing agent such as a hydroquinone, a 3-pyrazolidone derivative or an aminophenol derivative, etc., may be incorporated into the photographic light-sensitive material.

The present invention is illustrated in greater detail by reference to the following examples, but the present invention is not to be construed as being limited thereto.

EXAMPLE 1

On a paper support, both surfaces of which were laminated with polyethylene, was coated a coating solution comprising silver chlorobromide (silver bromide: 90 mol%; coating amount of silver: 720 mg/m$^2$), gelatin (2,000 mg/m²) and a dispersion of a 4-equivalent magenta coupler, i.e., 1-(2,4,6-trichlorophenyl)-3-(2-chloro-5-tetradecanamido)anilino-2-pyrazolin-5-one (600 mg/m²) and 2,5-di-tert-octyl hydroquinone (80 mg/m²) together with a coupler solvent, i.e., o-cresyl phosphate (800 mg/m²). On this emulsion layer was coated a gelatin protective layer (1,000 mg/m²) to prepare Sample 1.

Using an equimolar amount of the 2-equivalent magenta couplers according to the present invention, i.e., Couplers I-19, I-36, I-44 and I-46 in place of the 4-equivalent magenta coupler and reducing the coating amount of silver halide to one half of that in Sample 1, Samples 2, 5, 8 and 11 were prepared, respectively. Further, the heterocyclic amino compound according to the present invention, i.e., Compound 1, was added to the coating solution in an equimolar amount of the coupler to prepare Samples 3, 6, 9 and 12, respectively. Moreover, the heterocyclic amino compound according to the present invention, i.e., Compound 2, was added to the coating solution in an equimolar amount of the coupler to prepare Samples 4, 7, 10 and 13, respectively.

These samples were exposed to light through an optical wedge and processed according to the following steps:

| Processing Step (33° C.) | |
| --- | --- |
| Color Development | 3 min 30 sec |
| Bleach-Fixing | 1 min 30 sec |
| Washing with Water | 3 min |
| Drying (at 50° C. to 80° C.) | 2 min |

The composition of each processing solution was set forth below:

| Color Developing Solution: | |
| --- | --- |
| Benzyl Alcohol | 12 ml |
| Diethylene Glycol | 5 ml |
| Potassium Carbonate | 25 g |
| Sodium Chloride | 0.1 g |
| Sodium Bromide | 0.5 g |
| Anhydrous Sodium Sulfite | 2 g |
| Hydroxylamine Sulfate | 2 g |
| Fluorescent Whitening Agent | 1 g |
| N—Ethyl-N—β-methanesulfonamidoethyl-3-methyl-4-aminoaniline Sulfate | 4 g |
| Water to make | 1 liter |
| Sodium hydroxide was added to adjust the pH to 10.2 | |
| Bleach-Fixing Solution: | |
| Ammonium Thiosulfate | 124.5 g |
| Sodium Metabisulfite | 13.3 g |
| Anhydrous Sodium Sulfite | 2.7 g |
| Iron (III) Ammonium Ethylenediaminetetraacetate | 65 g |
| Color Developing Solution (as described above) | 100 ml |
| Adjustment of pH to 6.7 to 6.8 | |
| Water to make | 1 liter |

The development processing was carried out using a conventional roller transportation type development machine using a conventional replenishment procedure. Thus, the composition of the processing solutions used was in an equilibrium condition.

Then, the magenta reflective density in unexposed areas was measured using a Fuji type automatic recording densitometer setting Sample 1 as a standard. The results thus obtained are set forth in Table 1 below.

TABLE 1

| Sample | Magenta Coupler | Heterocyclic Amino Compound | Magenta Density |
| --- | --- | --- | --- |
| 1 (Comparison) | 4-equivalent | — | (0.00) |
| 2 (Comparison) | I-19 | — | +0.13 |
| 3 (Present Invention) | I-19 | 1 | 0.00 |
| 4 (Present Invention) | I-19 | 2 | +0.02 |
| 5 (Comparison) | I-36 | — | +0.24 |
| 6 (Present Invention) | I-36 | 1 | +0.01 |
| 7 (Present Invention) | I-36 | 2 | +0.04 |
| 8 (Comparison) | I-44 | — | +0.10 |
| 9 (Present Invention) | I-44 | 1 | 0.00 |
| 10 (Present Invention) | I-44 | 2 | +0.01 |
| 11 (Comparison) | I-46 | — | +0.16 |
| 12 (Present Invention) | I-46 | 1 | 0.00 |
| 13 (Present Invention) | I-46 | 2 | +0.03 |

From the results shown in Table 1 it is apparent that the magenta stain formed by development processing can be prevented by the combined use of the 2-equivalent magenta coupler and the heterocyclic amino compound according to the present invention.

EXAMPLE 2

On a paper support, both surfaces of which were laminated with polyethylene, were coated a first layer (undermost layer) to a sixth layer (uppermost layer) as shown below in order to prepare a multilayer color photographic light-sensitive material which was designated Sample A. In the Table below the coating amounts are set forth in mg/m².

| | |
| --- | --- |
| Sixth Layer: (protective layer) | Gelatin (1,500 mg/m²) |
| Fifth Layer: (red-sensitive layer) | Silver chlorobromide emulsion (silver bromide: 50 mol %; silver: 250 mg/m²) Gelatin (1,500 mg/m²) Cyan coupler*¹ (500 mg/m²) Coupler solvent*² (250 mg/m²) |
| Fourth Layer: (ultraviolet light-absorbing layer) | Gelatin (1,200 mg/m²) Ultraviolet light-absorbing agent*³ (700 mg/m²) Ultraviolet light-absorbing agent solvent*² (250 mg/m²) |
| Third Layer: (green-sensitive layer) | Silver chlorobromide emulsion (silver bromide: 70 mol %; silver: 350 mg/m²) Gelatin (1,500 mg/m²) Magenta coupler*⁴ (400 mg/m²) Coupler solvent*⁵ (400 mg/m²) |
| Second Layer: (interlayer) | Gelatin (1,000 mg/m²) |
| First Layer: (blue-sensitive layer) | Silver chlorobromide emulsion (silver bromide: 80 mol %; silver: 350 mg/m²) Gelatin (1,500 mg/m²) Yellow coupler*⁶ (500 mg/m²) Coupler solvent*² (500 mg/m²) |
| Support: | Paper support both surfaces of which were laminated with polyethylene [white pigment (TiO₂, etc.) and bluish dye (ultramarine blue, etc.) were incorporated into the polyethylene layer of the First Layer side] |

*¹Cyan coupler: 2-[α-(2,4-Di-tert-amylphenoxy)-butanamido]-4,6-dichloro-5-methyl-phenol
*²Solvent: Trinonyl phosphate
*³Ultraviolet light-absorbing agent: 2-(2-Hydroxy-3-sec-butyl-5-tert-butylphenyl)-benzotriazole
*⁴Magenta coupler: 1-(2,4,6-Trichlorophenyl)-3-(2-chloro-5-tetradecanamido)anilino-2-pyrazolin-5-one
*⁵Coupler solvent: Tri-o-cresyl phosphate
*⁶Yellow coupler: α-Pivaloyl-α-(2,4-dioxo-5,5'-dimethyloxazolidin-3-yl)-2-chloro-5-[α-(2,4-di-tert-amylphenoxy)-butanamido]acetanilide Sample B was prepared in the same manner as described in Sample A except that 500 mg/m² of Coupler I-43 as a magenta coupler and 175 mg/m² of the silver chlorobromide emulsion were used in the third layer. Further, 50 mol% of di-tert-octyl hydroquinone (comparison compound) per the coupler, 150 mg/m² of sulfinic acid polymer (comparison compound) of the formula:

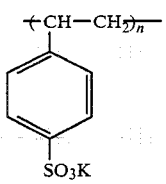

and 100 mol% of Compounds 1, 2, 3 and 22 according to the present invention per the coupler were added to the third layer of Sample B to prepare Samples C, D, E, F, G and H, respectively.

These samples were exposed to light through an optical wedge and subjected to the same processing steps as described in Example 1. The magenta reflective density in the unexposed areas was measured and the difference in density from that of Comparison Sample A was calculated. The results thus obtained are shown in Table 2 below.

TABLE 2

| Sample | Magenta Coupler | Additive | Magenta Density | Sensitivity* |
|---|---|---|---|---|
| A (Comparison) | 4-equivalent | — | (0.00) | 100 |
| B (Comparison) | I-43 | — | +0.17 | 91 |
| C (Comparison) | I-43 | Di-tert-octyl hydroquinone | +0.13 | 83 |
| D (Comparison) | I-43 | Sulfinic acid polymer | +0.15 | 87 |
| E (Present Invention) | I-43 | Compound 1 | +0.00 | 97 |
| F (Present Invention) | I-43 | Compound 2 | +0.02 | 98 |
| G (Present Invention) | I-43 | Compound 3 | +0.03 | 100 |
| H (Present Invention) | I-43 | Compound 22 | +0.02 | 98 |

*Relative value when the sensitivity of Sample A is taken as 100.

It is apparent from the results shown in Table 2 that the compounds according to the present invention have an extremely good effect on preventing the formation of stain due to development processing of the photographic material containing 2-equivalent magenta couplers in comparison with known reducing agents such as a hydroquinone, etc. Furthermore, the compounds according to the present invention do not injure the photographic properties of the photographic light-sensitive materials.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having coated thereon at least one silver halide emulsion layer, the color photographic light-sensitive material having at least one layer containing at least one of 2-equivalent magenta coupler of the 5-pyrazolone type represented by the following general formula (I):

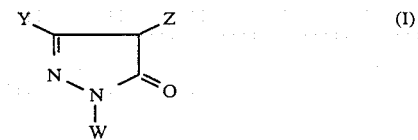

wherein W represents a phenyl group substituted with at least one substituent selected from the group consisting of a halogen atom, an alkyl group, an alkoxy group, an alkoxycarbonyl group and a cyano group; Y represents an acylamino group or an anilino group; and Z represents a group capable of being released upon coupling, and at least one compound represented by the following general formula (II):

wherein $R^1$ and $R^2$, which may be the same or different, each represents a hydrogen atom, an alkyl group or an aryl group, provided that both $R^1$ and $R^2$ do not represent hydrogen atoms at the same time; $Z^1$ represents a methine group or the group —N=; and Q represents an atomic group which contains a nitrogen atom, a sulfur atom or an oxygen atom and is necessary to form a 5-membered or a 6-membered heterocyclic ring together with the group

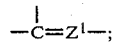

wherein the group capable of being released upon coupling represented by Z is an aryloxy group, an alkoxy group, a heterocyclic oxy group, a silyoxy group, a phosphonoxy group, an alkylthio group, an arylthio groups, a heterocyclic group, a heterocyclic thio group, an acylthio group, a thiocyano group, an aminothiocarbonylthio group, an acylamino group, a sulfonamido group, an alkoxycarbonylamino group, an aryloxycarbonylamino group or a nitrogen-containing heterocyclic group which is connected to the active position of the pyrazolone ring through the nitrogen atom; and wherein the aryl group represented by $R^1$ or $R^2$ is an aryl group having from 6 to 38 carbon atoms which may be substituted with a halogen atom, an aryl group, a heterocyclic group, a cyano group, an alkoxy group, an aryloxy group, an acylamino group, an imido group, an anilino group, an alkylamino group, a heterocyclic amino group, a ureido group, a sulfamoylamino group, an alkylthio group, an arylthio group, a heterocyclic thio group, an alkoxycarbonylamino group, an aryloxycarbonylamino group, a sulfonamido group, a carbamoyl group, a sulfamoyl group, a sulfonyl group, a sulfinyl group, an acyl group, an alkoxycarbonyl group, an aryloxycarbonyl group, a phosphonyl group, an imino group, a cyanothio group, an acyloxy group, a carbamoyloxy group, a silyloxy group, a sulfonyloxy group, a heterocyclic oxy group, a hydroxy group or a nitro group.

2. A silver halide color photographic light-sensitive material as claimed in claim 1, wherein the 2-equivalent magenta coupler represented by general formula (I) is represented by the following general formula (Ib):

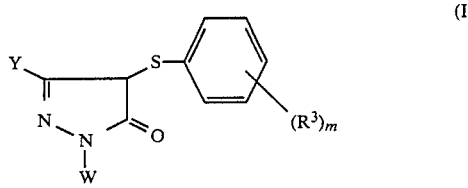

wherein W represents a phenyl group substituted with at least one substituent selected from the group consisting of a halogen atom, an alkyl group, an alkoxy group, an alkoxycarbonyl group and a cyano group; $R^3$ represents a hydrogen atom, a halogen atom, an acylamino group, a sulfonamido group, a carbamoyl group, a sulfamoyl group, an alkylthio group, an alkoxycarbonyl group, a hydroxy group, an alkyl group, an alkoxy group or an aryl group; m represents an integer of from 1 to 5 and when m is 2 or more, $R^3$'s may be the same or different; and Y represents an acylamino group or an anilino group.

3. A silver halide color photographic light-sensitive material as claimed in claim 2, wherein the 2-equivalent magenta coupler represented by the general formula (Ib) is represented by the following general formula (Ic):

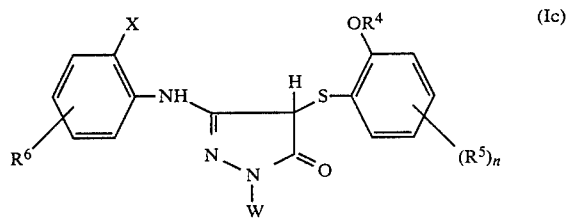

wherein W has the same meaning as defined in general formula (Ib); $R^4$ represents an alkyl group or an aryl group; X represents a halogen atom or an alkoxy group; $R^5$ represents a hydrogen atom, a hydroxy group, a halogen atom, an alkyl group, an alkoxy group or an aryl group; $R^6$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group, or a trichloromethyl group; and n represents an integer of from 1 to 4.

4. A silver halide color photographic light-sensitive material as claimed in claim 3, wherein W represents a phenyl group substituted with at least one substituent selected from the group consisting of a halogen atom, an alkyl group having from 1 to 22 carbon atoms, an alkoxy group having from 1 to 22 carbon atoms, an alkoxycarbonyl group having from 2 to 23 carbon atoms and a cyano group; $R^4$ represents an alkyl group having from 1 to 22 carbon atoms or an aryl group; X represents a halogen atom or an alkoxy group having from 1 to 22 carbon atoms; $R^6$ represents a hydrogen atom, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, an alkylureido group, an acyl group, a nitro group, a carboxy group, or a trichloromethyl group, wherein the alkyl moiety has from 1 to 36 carbon atoms and the aryl moiety has from 6 to 36 carbon atoms; $R^5$ represents a hydrogen atom, a hydroxy group, a halogen atom, an alkyl group having 1 to 36 carbon atoms, an alkoxy group having 1 to 36 carbon atoms or an aryl group having 6 to 36 carbon atoms.

5. A silver halide color photographic light-sensitive material as claimed in claim 3, wherein the total number of carbon atoms included in the groups represented by $R^4$ and $R^5$ is not less than 6.

6. A silver halide color photographic light-sensitive material as claimed in claim 1, wherein a substituent for the substituted methine group represented by Z' is an alkyl group, an aryl group, a halogen atom, an alkoxy group, an acylamino group, an imido group, a sulfonamido group, a carbamoyl group, a sulfamoyl group, an alkoxycarbonyl group, an alkylsulfonyl group, an alkylthio group or a hydroxy group.

7. A silver halide color photographic light-sensitive material as claimed in claim 6, wherein the alkyl group is an alkyl group as defined for $R^1$ or $R^2$ in claim 1.

8. A silver halide color photographic light-sensitive material as claimed in claim 6, wherein the aryl group is an aryl group as defined for $R^1$ or $R^2$ in claim 1.

9. A silver halide color photographic light-sensitive material as claimed in claim 1, wherein the compound represented by general formula (II) is represented by the following general formula (III):

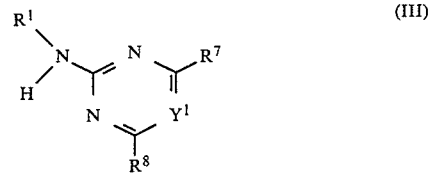

wherein $R^1$ has the same meaning as defined for $R^1$ in claim 1; $R^7$ and $R^8$ each represents a hydrogen atom, an alkyl group as defined for $R^1$ or $R^2$ in claim 1, an aryl group as defined for $R^1$ or $R^2$ in claim 1, a halogen atom, a heterocyclic group, a cyano group, an alkoxy group, an aryloxy group, an acylamino group, a heterocyclic oxy group, an imido group, an anilino group, an alkylamino group, a heterocyclic amino group, a ureido group, a sulfamoylamino group, an alkylthio group, an arylthio group, a heterocyclic thio group, an alkoxycarbonylamino group, an aryloxycarbonylamino group, a sulfonamido group, a carbamoyl group, a sulfamoyl group, a sulfonyl group, a sulfinyl group, an acyl group, an alkoxycarbonyl group, an aryloxycarbonyl group, a phosphonyl group, an imino group, a cyanothio group, an acyloxy group, a carbamoyloxy group, a hydroxy group, a silyloxy group, a sulfonyloxy group or a nitro group; and $Y^1$ represents a methine group, the group

where $R^7$ is as above defined, or the group —N=.

10. A silver halide color photographic light-sensitive material as claimed in claim 9, wherein the compound represented by general formula (III) is represented by the following general formula (IV):

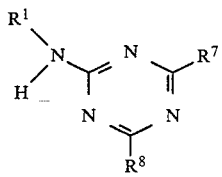

wherein $R^1$, $R^7$ and $R^8$ each has the same meaning as defined for $R^1$, $R^7$ and $R^8$ in claim 9.

11. A silver halide color photographic light-sensitive material as claimed in claim 10, wherein the compound represented by general formula (IV) is represented by the following general formula (V):

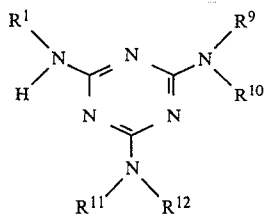

wherein $R^1$ has the same meaning as defined for $R^1$ in claim 10, and $R^9$, $R^{10}$, $R^{11}$ and $R^{12}$ each has the same meaning as defined for $R^1$ or $R^2$ in claim 1.

12. A silver halide color photographic light-sensitive material as claimed in claim 1, wherein the amount of the compound represented by general formula (II) is from 0.05 mol to 5 mols per mol of the 2-equivalent magenta coupler represented by general formula (I).

13. A silver halide color photographic light-sensitive material as claimed in claim 1, wherein the amount of the compound represented by general formula (II) is 0.5 mol to 3 mols per mol of the 2-equivalent magenta coupler represented by general formula (I).

14. A silver halide color photographic light-sensitive material as claimed in claim 1, wherein the layer containing the 2-equivalent magenta coupler represented by general formula (I) and the compound represented by general formula (II) is a silver halide emulsion layer.

15. A silver halide color photographic light-sensitive material as claimed in claim 14, wherein the silver halide emulsion layer is a green-sensitive silver halide emulsion layer.

16. A silver halide color photographic light-sensitive material as claimed in claim 15, wherein the photographic material further comprises a blue-sensitive silver halide emulsion layer containing a yellow color forming coupler and a red-sensitive silver halide emulsion layer containing a cyan color forming coupler.

17. A silver halide color photographic light-sensitive material as claimed in claim 16, wherein the photographic material is a color print paper.

18. A silver halide color photographic light-sensitive material as claimed in claim 1, wherein the alkyl group represented by $R^1$ or $R^2$ is a straight chain or branched chain alkyl group having from 1 to 32 carbon atoms, an aralkyl group, an alkenyl group, a cycloalkyl group, a cycloalkenyl group or an alkynyl group each of which may be substituted with a halogen atom, an aryl group, a heterocyclic group, a cyano group, an alkoxy group, an aryloxy group, an acylamino group, an imido group, an anilino group, an alkylamino group, a heterocyclic amino group, a ureido group, a sulfamoylamino group, an alkylthio group, an arylthio group, a heterocyclic thio group, an alkoxycarbonylamino group, an aryloxycarbonylamino group, a sulfonamido group, a carbamoyl group, a sulfamoyl group, a sulfonyl group, a sulfinyl group, an acyl group, an alkoxycarbonyl group, a aryloxycarbonyl group, a phosphonyl group, an imino group, a cyanothio group, an acyloxy group, a carbamoyloxy group, a silyloxy group, a sulfonyloxy group, a heterocyclic oxy group, a hydroxy group or a nitro group.

19. A method of forming a color image comprising developing an imagewise exposed silver halide color photographic light-sensitive material comprising a support having coated thereon at least one silver halide emulsion layer, the color photographic light-sensitive material having at least one layer containing at least one 2-equivalent magenta coupler of the 5-pyrazolone type represented by the following general formula (I):

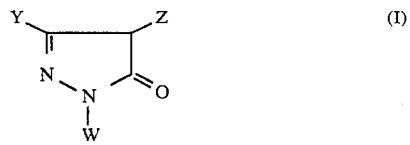

wherein W represents a phenyl group substituted with at least one substituent selected from the group consisting of a halogen atom, an alkyl group, an alkoxy group, an alkoxycarbonyl group and a cyano group; Y represents an acylamino group or an anilino group; and Z represents a group capable of being released upon coupling, and at least one compound represented by the following general formula (II):

wherein $R^1$ and $R^2$, which may be the same or different, each represents a hydrogen atom, an alkyl group or an aryl group, provided that both $R^1$ and $R^2$ do not represent hydrogen atoms at the same time; $Z^1$ represents a methine group, a substituted methine group or the group —N=; and Q represents an atomic group which contains a nitrogen atom, a sulfur atom or an oxygen atom and is necessary to form a 5-membered or a 6-membered heterocyclic ring together with the group

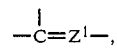

with an aqueous alkaline solution containing a color developing agent;

wherein the group capable of being released upon coupling represented by Z is an aryloxy group, an alkoxy group, a heterocyclic oxy group, a silyoxy group, a phosphonoxy group, an alkylthio group, an arylthio group, a heterocyclic thio group, an acylthio group, a thiocyano group, an aminothiocarbonylthio group, an acylamino group, a suflonamido group, an alkoxycarbonylamino group, an aryloxycarbonylamino group or a nitrogen-containing heterocyclic group which is connected to the active position of the pyrazolone ring through the nitrogen atom; and wherein the aryl group represented by $R^1$ or $R^2$ is an aryl group having from 6 to 38 carbon atoms which may be substituted with a halogen atom, an aryl group, a heterocyclic group, a cyano group, an alkoxy group, an aryloxy group, an acylamino group, an imido group, an anilino group, an alkylamino group, a heterocyclic amino group, a ureido group, a sulfamoylamino group, an alkylthio group, an arylthio group, a heterocyclic thio group, an alkoxycarbonylamino group, an aryloxycarbonylamino group, a sulfonamido group, a carbamoyl group, a sulfamoyl group, a sulfonyl group, a sulfinyl group, an acyl group, an alkoxycarbonyl group, an aryloxycarbonyl group, a phosphonyl group, an imino group, a cyanothio group, an acyloxy group, carbamoyloxy group, a silyloxy group, a sulfonyloxy group, a heterocyclic oxy group, a hydroxy group or a nitro group.

20. A method of forming a color image as claimed in claim 19, wherein the photographic material is, after color development, processed in a bleach-fixing solution.

21. A method of forming a color image as claimed in claim 20, wherein the color development step and the bleach-fixing step are carried out continuously.

* * * * *